US012721628B2

(12) United States Patent
Hannah et al.

(10) Patent No.: US 12,721,628 B2
(45) Date of Patent: Sep. 1, 2026

(54) COMPRESSION STAPLE INSERTION KIT

(71) Applicant: Tyber Medical LLC, Bethlehem, PA (US)

(72) Inventors: David Hannah, Nazareth, PA (US); John Abraham Perryman, Columbia, TN (US); Logan Schlecher, Slatington, PA (US); Daniel Ruba, Downingtown, PA (US)

(73) Assignee: Tyber Medical LLC, Bethlehem, PA (US)

( * ) Notice: Subject to any disclaimer, the term of this patent is extended or adjusted under 35 U.S.C. 154(b) by 0 days.

(21) Appl. No.: 18/575,355

(22) PCT Filed: Jun. 30, 2022

(86) PCT No.: PCT/US2022/035656
§ 371 (c)(1),
(2) Date: Dec. 29, 2023

(87) PCT Pub. No.: WO2023/278655
PCT Pub. Date: Jan. 5, 2023

(65) Prior Publication Data

US 2024/0315696 A1 Sep. 26, 2024

Related U.S. Application Data

(60) Provisional application No. 63/245,324, filed on Sep. 17, 2021, provisional application No. 63/221,497, (Continued)

(51) Int. Cl.
*A61B 17/10* (2006.01)
*A61B 17/064* (2006.01)
(Continued)

(52) U.S. Cl.
CPC .......... *A61B 17/10* (2013.01); *A61B 17/0642* (2013.01); *A61B 17/17* (2013.01); (Continued)

(58) Field of Classification Search
CPC ............ A61B 17/072; A61B 17/07207; A61B 17/064; A61B 17/0642; A61B 17/0682; (Continued)

(56) References Cited

U.S. PATENT DOCUMENTS 1,063,982 A 6/1913 Larnce
7,635,367 B2 12/2009 Groiso
(Continued)

OTHER PUBLICATIONS

PCT/US2022/035656 International Search Report and Written Opinion mailed Oct. 5, 2022.

*Primary Examiner* — Marcela I. Shirsat
(74) *Attorney, Agent, or Firm* — Joseph E. Maenner; Maenner & Associates, LLC

(57) ABSTRACT

A compression staple insertion kit includes first and second elongate handles, each including a handle arm having a proximal end and a distal end, distal from the proximal end. A boss extend is outwardly from the distal end. A central longitudinal axis extends between the arms. The handle arms are pivotally attached to each other at the distal ends at a pivot, which extends along the central longitudinal axis. A slider is slidingly attached to the handle. The slider is movable between a staple securing position at the distal end, wherein proximal ends are biased toward each other and a staple release position toward the proximal end, wherein the proximal ends are biased away from each other. A staple is disposed over the bosses.

18 Claims, 21 Drawing Sheets

Related U.S. Application Data filed on Jul. 14, 2021, provisional application No. 63/217,305, filed on Jul. 1, 2021.

(51) Int. Cl.
*A61B 17/068* (2006.01)
*A61B 17/072* (2006.01)
*A61B 17/076* (2006.01)
*A61B 17/17* (2006.01)
*A61B 90/00* (2016.01)

(52) U.S. Cl.
CPC ..... *A61B 17/064* (2013.01); *A61B 2017/0645* (2013.01); *A61B 17/068* (2013.01); *A61B 17/0682* (2013.01); *A61B 2017/0688* (2013.01); *A61B 2017/07271* (2013.01); *A61B 2017/07278* (2013.01); *A61B 17/076* (2013.01); *A61B 2090/037* (2016.02); *A61B 2090/0807* (2016.02)

(58) Field of Classification Search
CPC ....... A61B 17/10; A61B 17/17; A61B 17/076; A61B 17/068; A61B 2017/07271; A61B 2017/07278; A61B 2017/0645; A61B 2017/0688; A61B 2090/037; A61B 2090/0807
USPC ... 606/219, 215, 220, 96, 280, 299, 300, 75, 606/324, 76–78, 86 R, 86 A, 86 B, 916, 606/911
See application file for complete search history.

(56) References Cited

U.S. PATENT DOCUMENTS 7,699,203 B2 4/2010 McBride et al.
8,137,351 B2 3/2012 Prandi
8,211,109 B2 7/2012 Groiso
8,235,995 B2 8/2012 Focht et al.
8,372,075 B2 2/2013 Groiso
8,584,853 B2 11/2013 Knight et al.
8,596,514 B2 12/2013 Miller et al.
8,864,764 B2 10/2014 Groiso
9,017,331 B2 4/2015 Fox
9,034,037 B2 5/2015 Fiere et al.
9,039,737 B2 5/2015 Vold et al.
9,339,268 B2 5/2016 Fox
9,468,436 B2 10/2016 Groiso
9,486,212 B2 11/2016 Miller et al.
9,498,265 B2 11/2016 Sammarco
9,549,735 B2 1/2017 Shelton, IV et al.
9,675,344 B2 6/2017 Combrowski et al.
9,713,484 B2 7/2017 Sammarco
9,855,036 B2 1/2018 Palmer et al.
9,861,357 B2 1/2018 Palmer et al.
9,872,681 B2 1/2018 Miller et al.
9,907,551 B2 3/2018 Seavey et al.
9,931,115 B2 4/2018 Morgan et al.
10,010,320 B2 7/2018 Wahl
10,010,321 B2 7/2018 Cocaign
10,016,198 B2 7/2018 Morgan et al.
10,052,103 B2 8/2018 Wahl
10,064,619 B2 9/2018 Morgan et al.
10,105,134 B2 10/2018 Biedermann et al.
10,130,358 B2 11/2018 Palmer
10,166,022 B2 1/2019 Early et al.
10,188,388 B2 1/2019 Handie
10,226,286 B2 3/2019 Sammarco
10,492,841 B2 12/2019 Hartdegen et al.
10,507,021 B2 12/2019 Miller et al.
10,512,459 B2 12/2019 Fox
10,588,628 B2 3/2020 Vasta
10,610,218 B2 4/2020 Palmer et al.
10,610,221 B2 4/2020 Wahl
10,610,222 B2 4/2020 WAhl
10,716,562 B2 7/2020 Miller
10,842,487 B2 11/2020 Ritz et al.
10,874,389 B2 12/2020 Biedermann et al.
10,888,319 B2 1/2021 Vasta
11,006,948 B2 5/2021 Majors et al.
11,090,043 B2 8/2021 Biedermann et al.
11,337,695 B2 5/2022 Ye et al.
11,382,619 B2 7/2022 Wahl
2009/0254090 A1 10/2009 Lizee
2010/0133316 A1 6/2010 Lizee et al.
2013/0213843 A1* 8/2013 Knight ...................... A61L 2/26 434/262
2014/0276830 A1 9/2014 Cheney
2014/0276881 A1 9/2014 Taylor
2015/0230843 A1 8/2015 Palmer et al.
2017/0000482 A1* 1/2017 Averous ............. A61B 17/0642
2018/0353172 A1* 12/2018 Hartdegen ........... A61B 17/809
2019/0142415 A1* 5/2019 Valiani ................. A61B 17/068 227/177.1
2019/0192160 A1* 6/2019 Stamp ................ A61B 17/0682
2020/0000464 A1 1/2020 Gaston et al.
2020/0038076 A1 2/2020 Amis et al.
2020/0100785 A1 4/2020 Miller et al.
2020/0138433 A1 5/2020 Fox
2020/0197005 A1 6/2020 Daniel
2020/0214700 A1 7/2020 Beidermann et al.
2020/0214701 A1 7/2020 Wahl
2020/0237366 A1 7/2020 Wahl
2020/0352564 A1 11/2020 Biedermann et al.
2021/0015482 A1 1/2021 Venturini et al.
2021/0228364 A1 7/2021 Cheney et al.

* cited by examiner 302
360
190
52
50
B 302
360
52
50

300
302
360
190
52
50

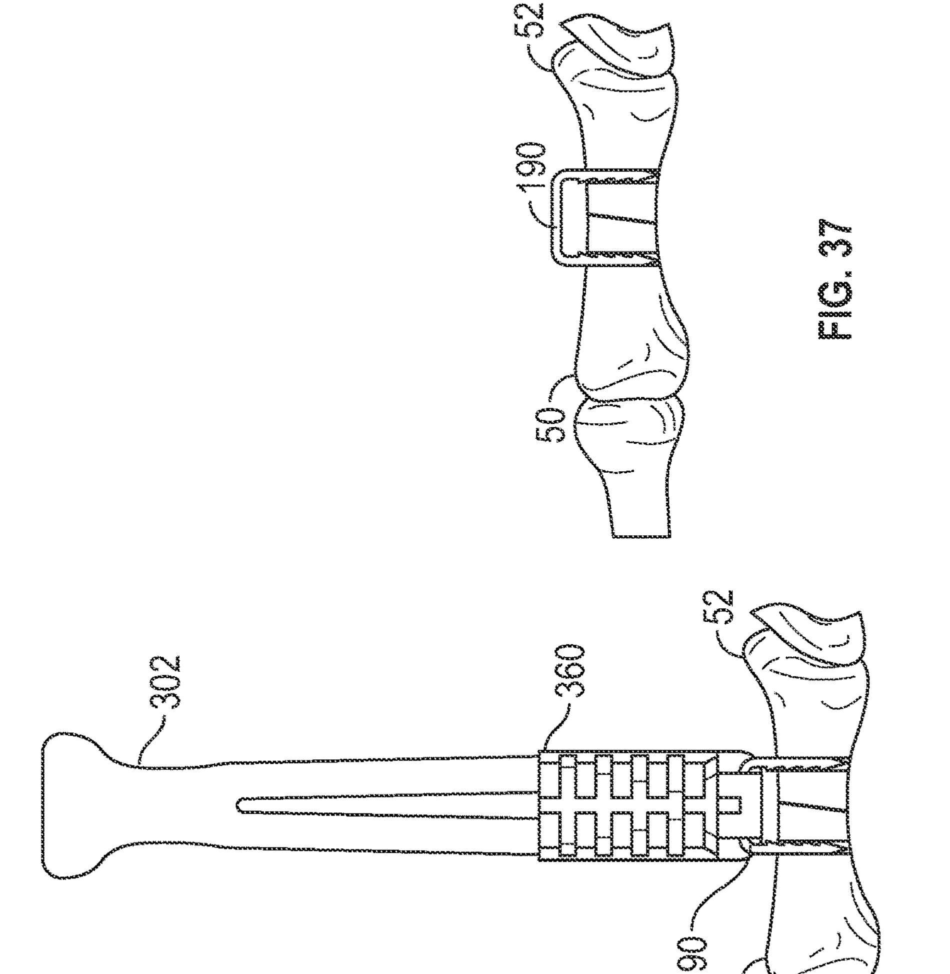
52
190
50
FIG. 37
302
360
52
190
50
FIG. 36
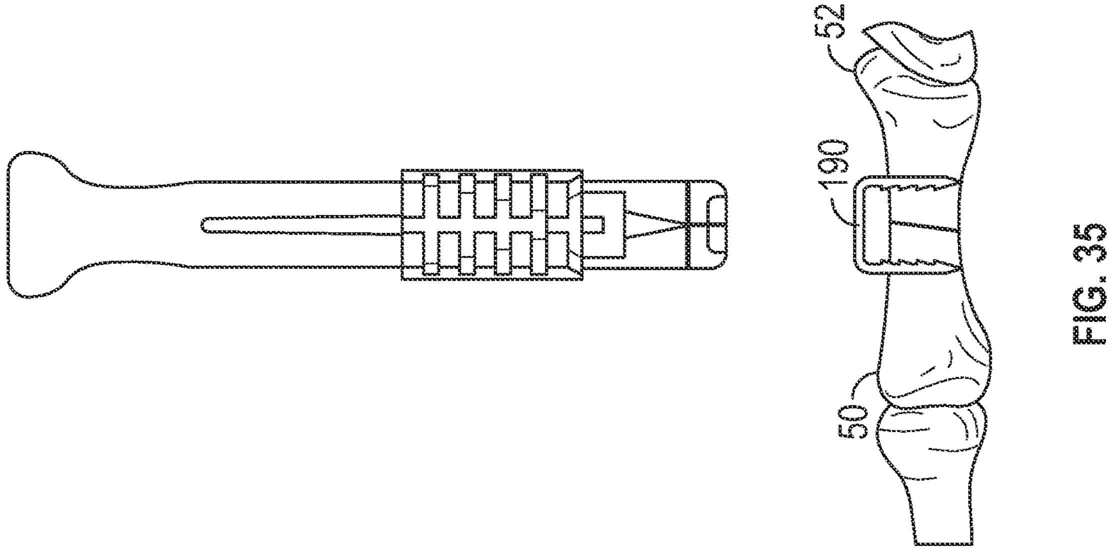
52
190
50
FIG. 35

400
404
402
406
410
412
414
420
194
477
190
192
C
C 400
404
402
412
D
410
414
406
194
192
E
E

COMPRESSION STAPLE INSERTION KIT

BACKGROUND OF THE INVENTION

Field of the Invention

The invention relates to compression staple insertion kits that can be single use or can be reloaded with additional staples after initial use.

Description of the Related Art

Staples are often used to secure adjacent bones or bone fragments together. Some inserters, however, cannot be reattached to the staple after the staple is deployed, either in transit or intra-operatively, requiring great effort to redeploy the staple or necessitating the use of another implant.

It would be beneficial to provide a staple inserter kit that allows a clinician to insert a staple into a patient without ever having to touch the staple and to be able to reattach the inserter to the staple if required.

SUMMARY OF THE INVENTION

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter.

In one embodiment, the present invention is a compression staple insertion kit that includes first and second elongate handles, each including a handle arm having a proximal end and a distal end, distal from the proximal end. A boss extend is outwardly from the distal end. A central longitudinal axis extends between the arms. The handle arms are pivotally attached to each other at the distal ends at a pivot, which extends along the central longitudinal axis. A slider is slidingly attached to the handle. The slider is movable between a staple securing position at the distal end, wherein proximal ends are biased toward each other and a staple release position toward the proximal end, wherein the proximal ends are biased away from each other. A staple is disposed over the bosses.

In an alternative embodiment, the present invention is a compression staple insertion kit comprising an elongate handle having a first handle arm having a first proximal end and a first distal end, distal from the first proximal end. A first boss extends outwardly from the first distal end. A second handle arm has a second proximal end and a second distal end, distal from the second proximal end. A second boss extends outwardly from the second distal end. A central longitudinal axis extends between the first handle arm and the second handle arm. The first handle arm is attached to the second handle arm at the first proximal end and the second proximal end. A slider is slidingly attached to the handle. The slider is movable between a staple securing position at the first distal end, wherein the first distal end and the second distal end are biased away from each other and the first boss is biased away from the second boss and a staple release position toward the first proximal end, wherein the first distal end and the second distal end are biased toward from each other and the first boss is biased toward from the second boss. A staple is disposed over the first boss and the second boss. The staple has a first arm, a second arm, and a bridge connecting the first arm and the second arm. The first boss is at a connection between the first arm and the bridge and wherein the second boss is at a connection between the second arm and the bridge.

Still alternatively, the present invention provides a compression staple insertion kit comprising an elongate handle having a handle proximate end and a handle distal end, distal from the handle proximate end. A lever arm has a lever proximal end and a lever distal end, distal from the lever proximal end. The lever distal end is attached to the handle distal end. A first boss extends from the handle distal end. A second boss extends from the lever distal end toward the first boss. When the lever proximal end is biased toward the handle proximal end, the first boss and the second boss are biased away from each other. A staple is disposed over the first boss and the second boss. The staple has a first arm, a second arm, and a bridge connecting the first arm and the second arm. The first boss is at a connection between the first arm and the bridge and the second boss is at a connection between the second arm and the bridge.

BRIEF DESCRIPTION OF THE DRAWINGS

The accompanying drawings, which are incorporated herein and constitute part of this specification, illustrate the presently preferred embodiments of the invention, and, together with the general description given above and the detailed description given below, serve to explain the features of the invention. In the drawings:

FIG. 35 is a side elevational view of the kit of FIG. 32, with the inserter removed from the staple;

FIG. 36 is a side elevational view of the inserter of FIG. 35 tamping the staple into the bone portions;

FIG. 37 is a side elevational view of the staple fully inserted into the bone portions;

DETAILED DESCRIPTION

Figures 1, 2:
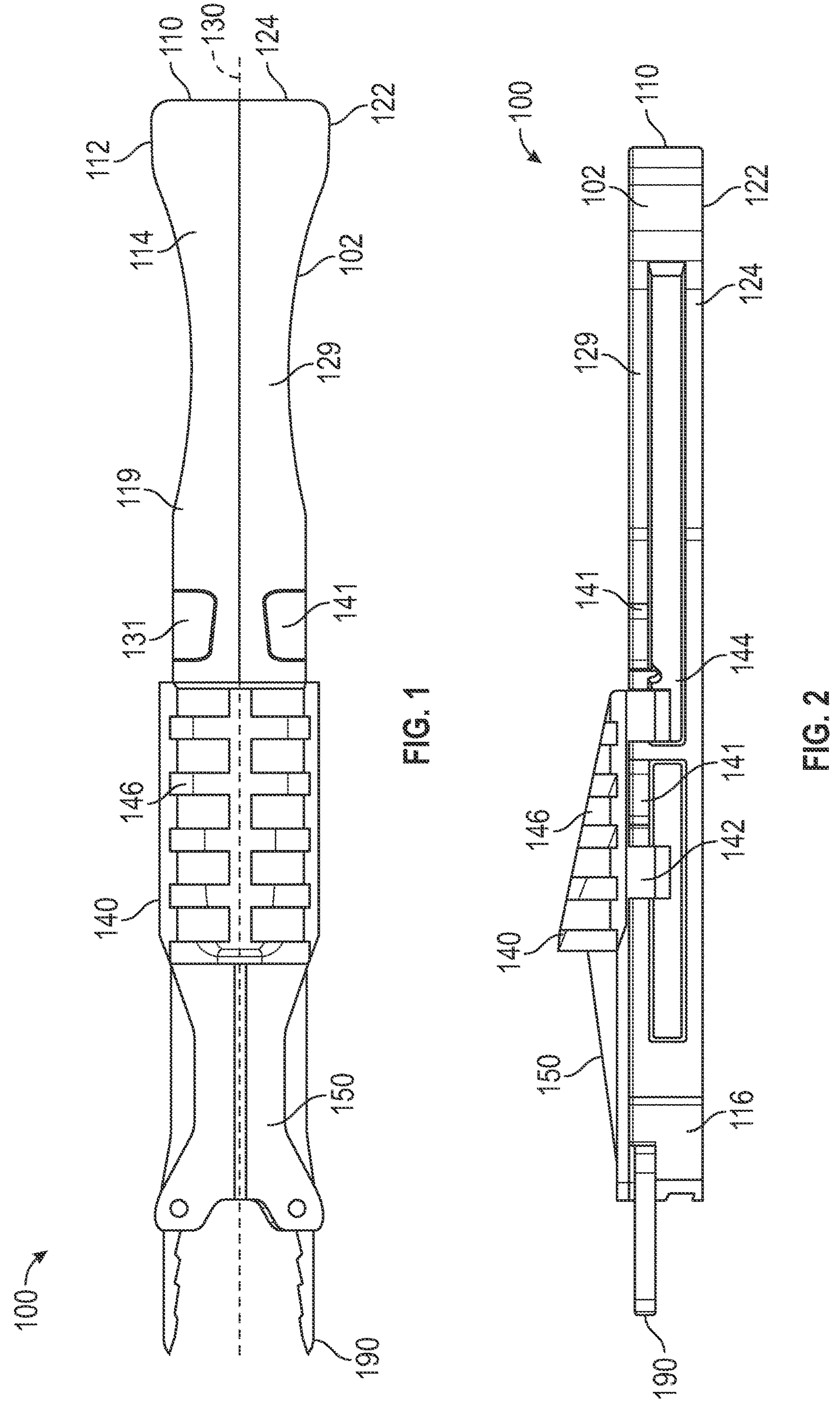
FIG. 1 is a top plan view of a staple inserter kit according to a first exemplary embodiment of the present invention, with the staple inserter in a pre-loaded position.
FIG. 2 is a side elevational view of the staple inserter kit of FIG. 1.
Figure 3:
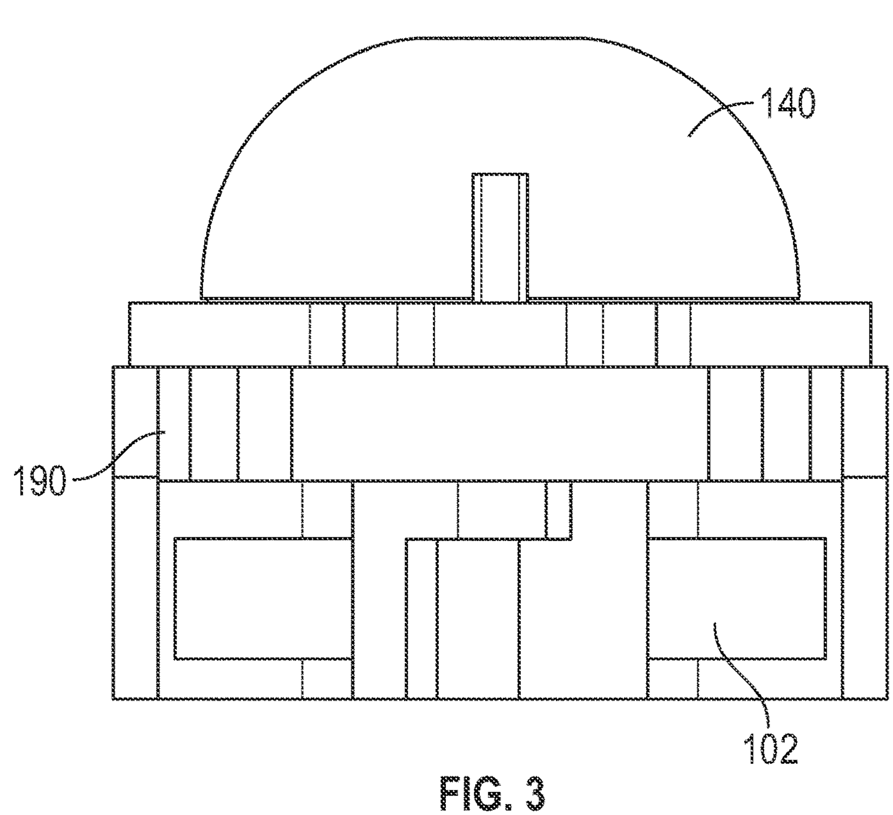
FIG. 3 is a front elevational view of the staple inserter kit of FIG. 1.
Figure 4:
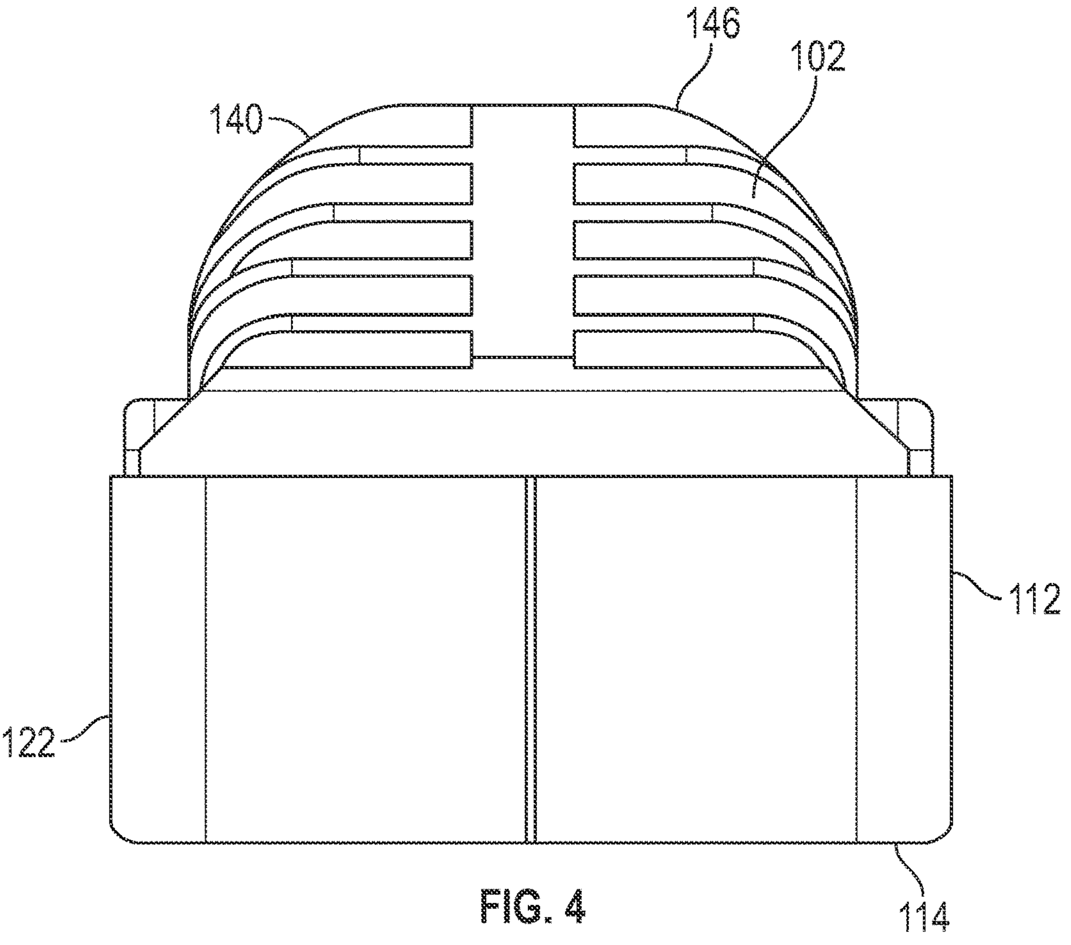
FIG. 4 is a rear elevational view of the staple inserter kit of FIG. 1.

In the drawings, like numerals indicate like elements throughout. Certain terminology is used herein for convenience only and is not to be taken as a limitation on the present invention. The terminology includes the words specifically mentioned, derivatives thereof and words of similar import. The embodiments illustrated below are not intended to be exhaustive or to limit the invention to the precise form disclosed. These embodiments are chosen and described to best explain the principle of the invention and its application and practical use and to enable others skilled in the art to best utilize the invention.

Reference herein to "one embodiment" or "an embodiment" means that a particular feature, structure, or characteristic described in connection with the embodiment can be included in at least one embodiment of the invention. The appearances of the phrase "in one embodiment" in various places in the specification are not necessarily all referring to the same embodiment, nor are separate or alternative embodiments necessarily mutually exclusive of other embodiments. The same applies to the term "implementation."

As used in this application, the word "exemplary" is used herein to mean serving as an example, instance, or illustration. Any aspect or design described herein as "exemplary" is not necessarily to be construed as preferred or advantageous over other aspects or designs. Rather, use of the word exemplary is intended to present concepts in a concrete fashion.

The word "about" is used herein to include a value of +/−10 percent of the numerical value modified by the word "about" and the word "generally" is used herein to mean "without regard to particulars or exceptions."

Additionally, the term "or" is intended to mean an inclusive "or" rather than an exclusive "or". That is, unless specified otherwise, or clear from context, "X employs A or B" is intended to mean any of the natural inclusive permutations. That is, if X employs A; X employs B; or X employs both A and B, then "X employs A or B" is satisfied under any of the foregoing instances. In addition, the articles "a" and "an" as used in this application and the appended claims should generally be construed to mean "one or more" unless specified otherwise or clear from context to be directed to a singular form.

Unless explicitly stated otherwise, each numerical value and range should be interpreted as being approximate as if the word "about" or "approximately" preceded the value of the value or range.

The use of figure numbers and/or figure reference labels in the claims is intended to identify one or more possible embodiments of the claimed subject matter in order to facilitate the interpretation of the claims. Such use is not to be construed as necessarily limiting the scope of those claims to the embodiments shown in the corresponding figures.

It should be understood that the steps of the exemplary methods set forth herein are not necessarily required to be performed in the order described, and the order of the steps of such methods should be understood to be merely exemplary. Likewise, additional steps may be included in such methods, and certain steps may be omitted or combined, in methods consistent with various embodiments of the present invention.

Although the elements in the following method claims, if any, are recited in a particular sequence with corresponding labeling, unless the claim recitations otherwise imply a particular sequence for implementing some or all of those elements, those elements are not necessarily intended to be limited to being implemented in that particular sequence.

Referring to FIGS. 1-11, a first exemplary embodiment of a compression staple insertion kit 100 is disclosed. Kit 100 provides a staple and an inserter that is used to insert the staple into adjacent bones or adjacent bone fragments. FIGS.

1-6 show kit 100, which includes an inserter 102 and a staple 190. Staple 190 can be pre-loaded onto inserter 102 prior to packaging kit 100.

Inserter 102 includes an elongate handle 110 having a first handle arm 112 having a first proximal end 114 and a first distal end 116, distal from the first proximal end 114. A first boss or pin 118 extends outwardly from the first distal end 116.

The first handle arm 112 also includes a slot 117 that extends along the side of first handle 110. The first handle arm 112 also includes a top surface 119 and the slot 117 extends to the top surface 119.

Similarly, a second handle arm 122 has a second proximal end 124 and a second distal end 126, distal from the second proximal end 124. A second boss or pin 128 extends outwardly from the second distal end 126.

The second handle arm 122 also includes a slot 127 that extends along the side of second handle arm 120. The second handle arm 122 also includes a top surface 129 and the slot 127 extends to the top surface 129.

A central longitudinal axis 130 extends between the first handle arm 112 and the second handle arm 122. The first handle arm 112 is pivotally attached to the second handle arm 122 at the first distal end 116 and the second distal end 126 at a pivot 132. The pivot 132 extends along the central longitudinal axis 130.

The first proximal end 114 is on a first side of the central longitudinal axis 130 and the first distal end 116 is on an opposing side of the central longitudinal axis 130. Similarly, the second proximal end 124 is on the opposing side of the central longitudinal axis 130 and the second distal end 126 is on the first side of the central longitudinal axis 130.

Figures 7, 8:
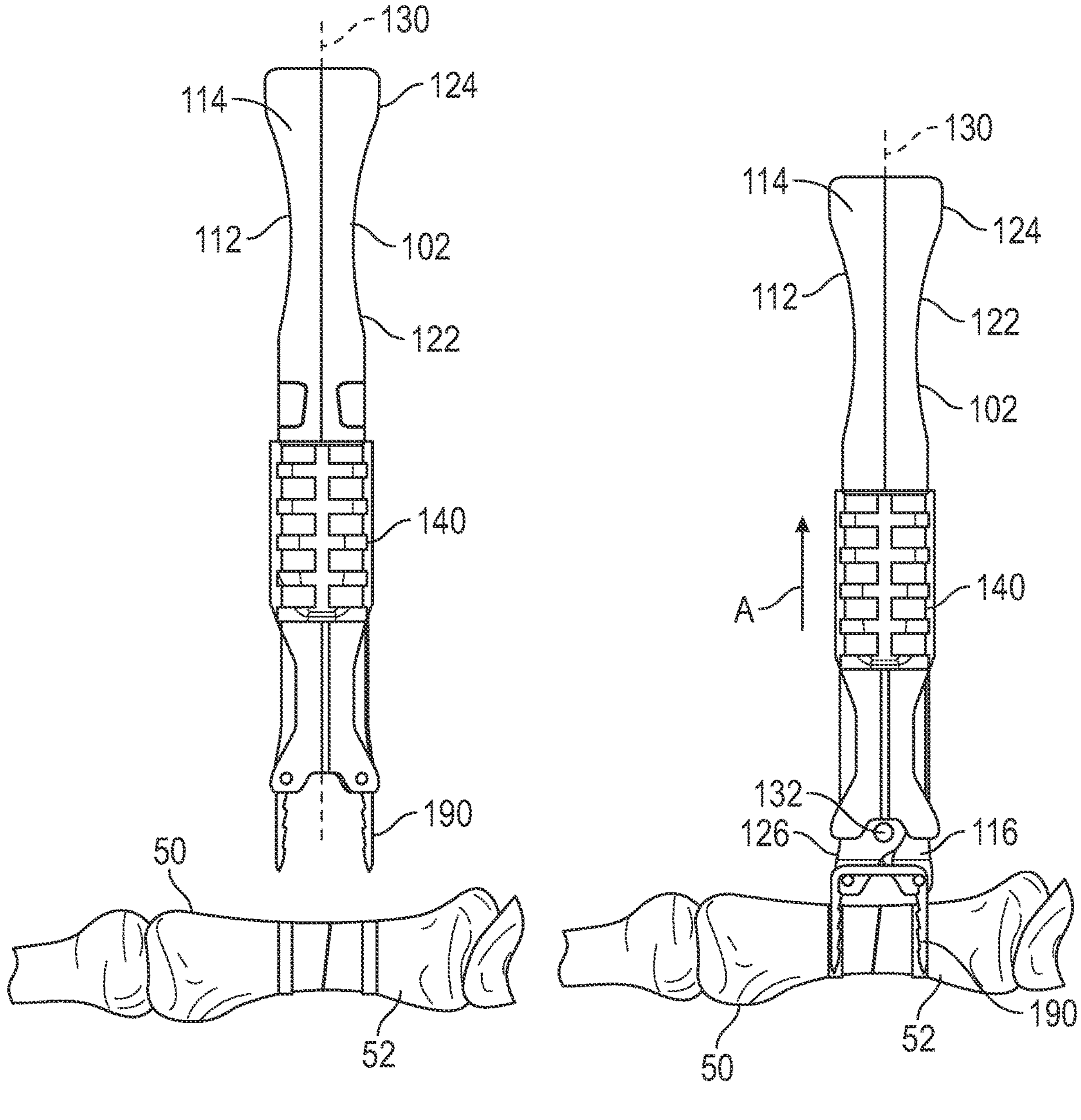
FIG. 7 is a side elevational view of the inserter kit of FIG. 1, with the staple being inserted into two adjacent bone portions.
FIG. 8 is a side elevational view of the inserter kit of FIG. 1, with the staple partially inserted into the bone portions.

A slider 140 is slidingly attached to the handle 102. The slider 140 is movable between a staple securing position at the first distal end 116, as shown in FIG. 8, where the first proximal end 114 and the second proximal end 124 are biased toward each other and the first pin 118 is biased away from the second pin 128; and a staple release position, shown in FIG. 9, toward the first proximal end 114, wherein the first proximal end 114 and the second proximal end 124 are biased away from each other and the first pin 118 is biased toward the second pin 128.

Figure 9:
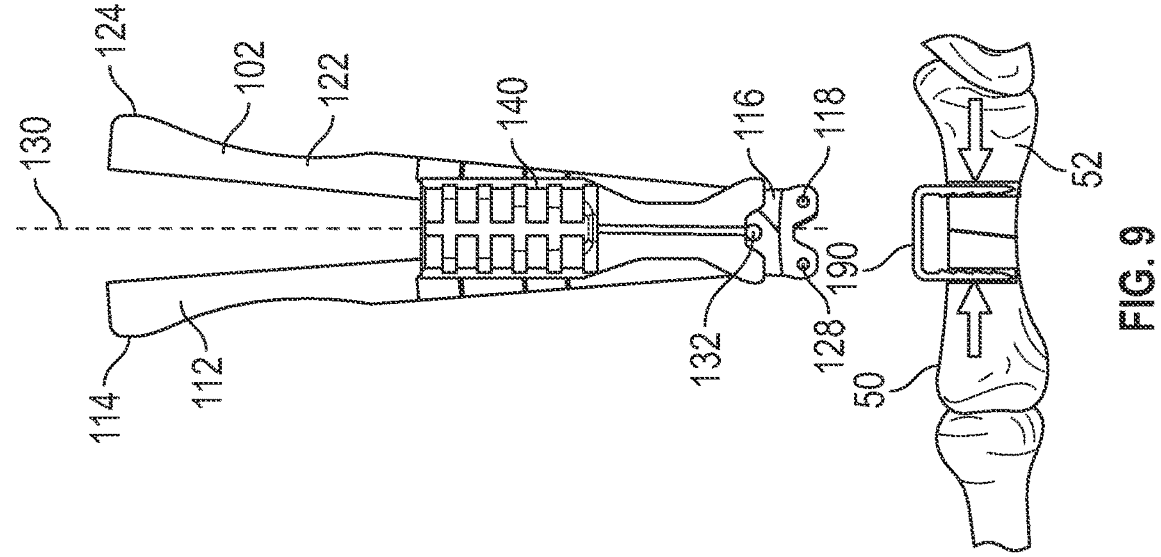
FIG. 9 is a side elevational view of the inserter kit of FIG. 1, with the inserter removed from the staple.
Figure 12:
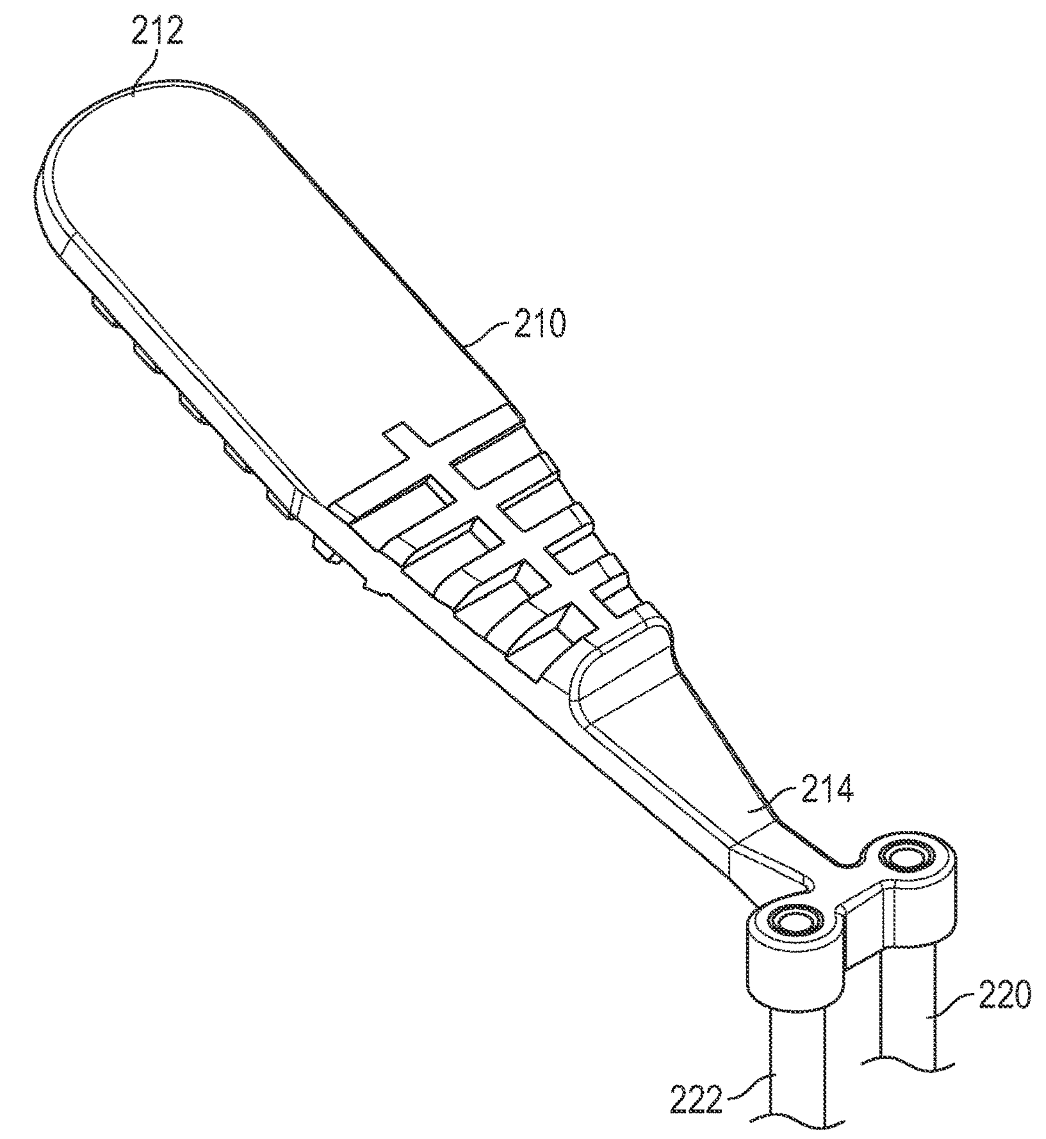
FIG. 12 is a perspective view of a staple drill guide according to an exemplary embodiment of the present invention.
Figure 13:
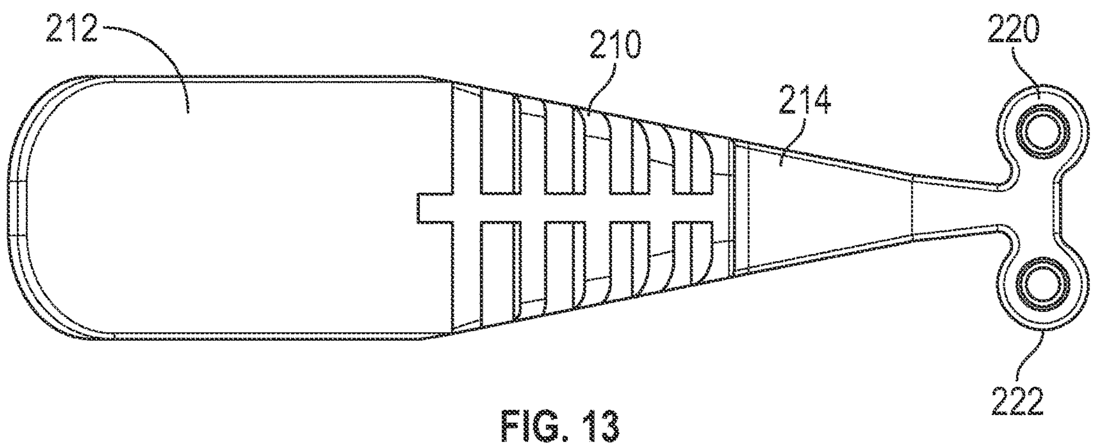
FIG. 13 is a top plan view of the guide of FIG. 12.
Figure 14:
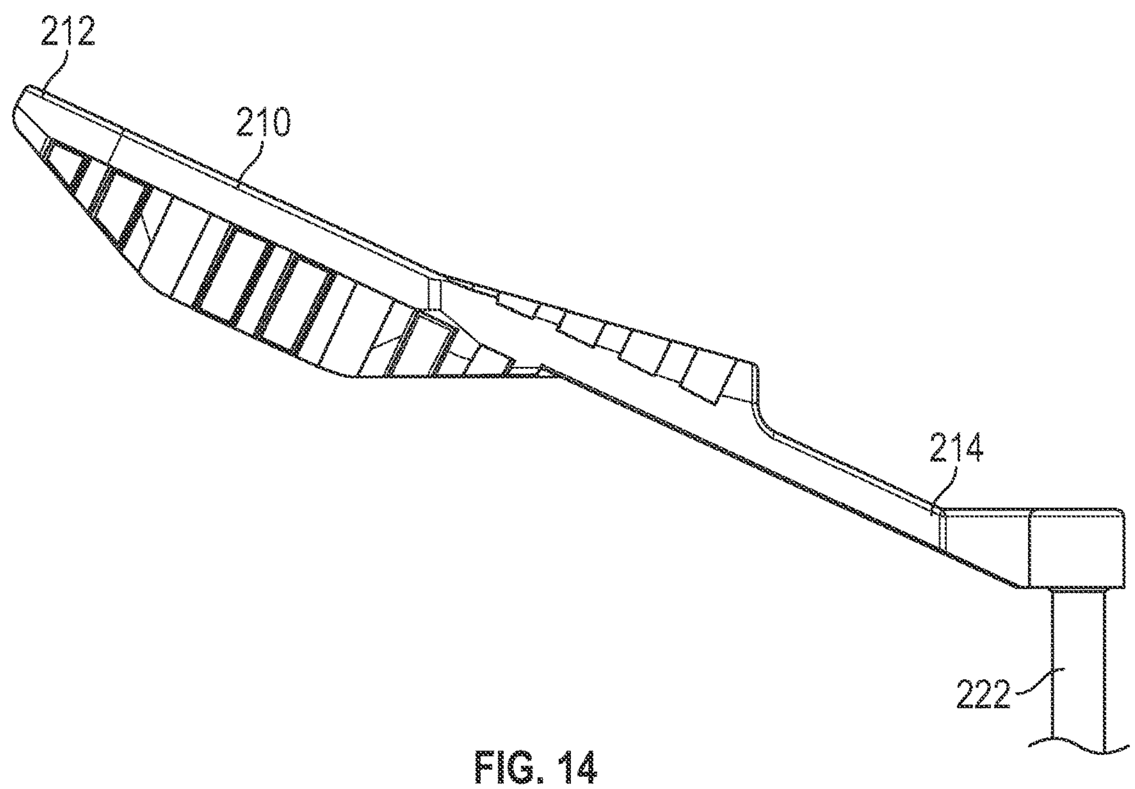
FIG. 14 is a side elevational view of the guide of FIG. 12.
Figure 15:
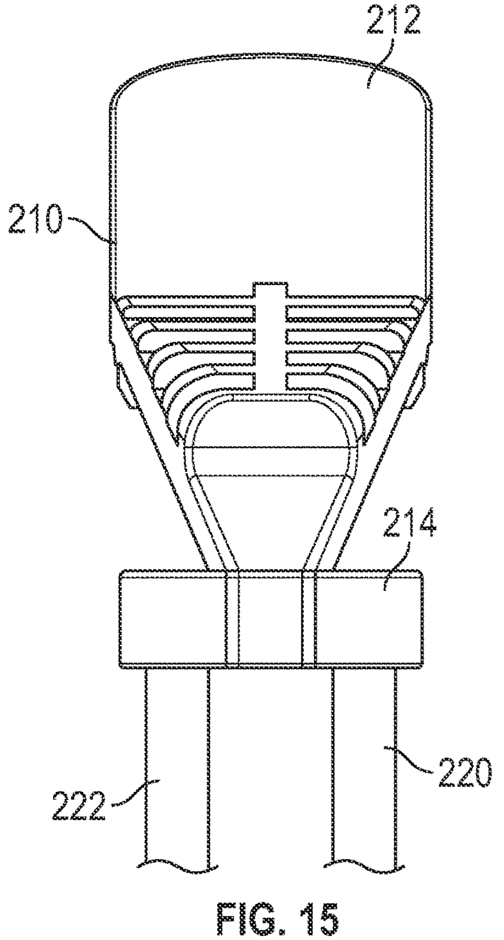
FIG. 15 is a front elevational view of the guide of FIG. 12.

The slider 140 includes guides 142, 144 that are configured to ride along the slot 117. When slider 140 is slid to a staple releasee position, as shown in FIG. 6, guides 142, 144 align with cutouts 141 in top surface 119, 129 in first handle arm 112 and second handle arm 122, respectively, and allow proximal ends 114, 124 of first handle arm 112 and second handle arm 122, respectively, to pivot away from each other, as shown in FIG. 9.

The slider 140 also includes a proximal ramp portion 146 that acts as a thumb guide to assist a clinician in sliding slide 140 along handle 110.

Figure 5:
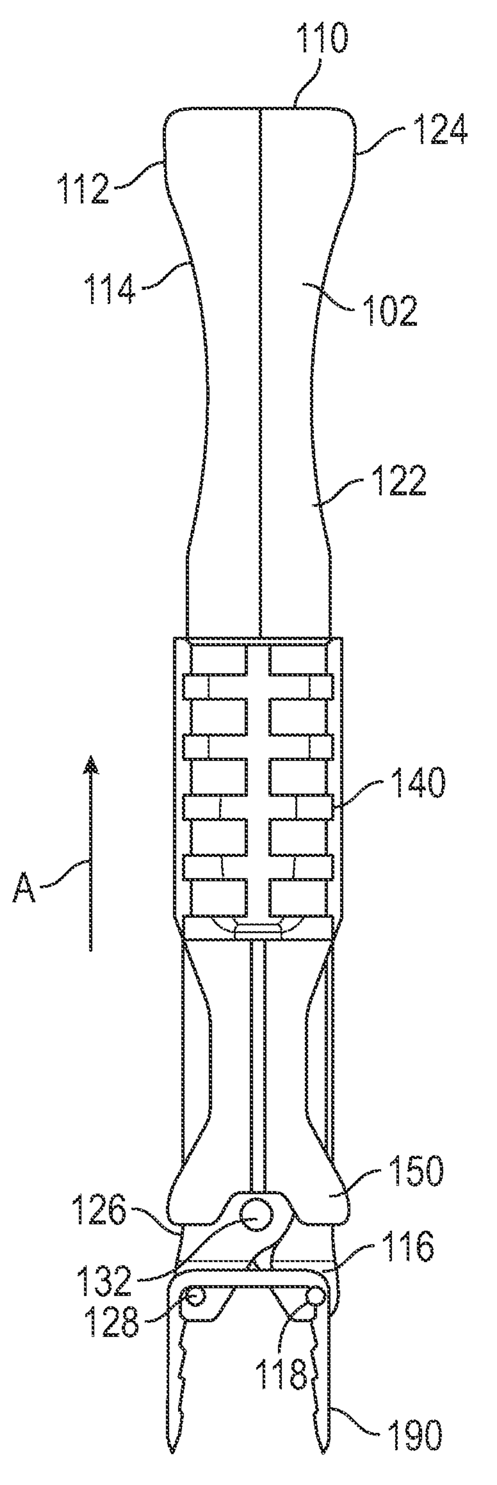
FIG. 5 is a top plan view of the staple inserter kit of FIG. 1, showing a slider on the inserter being moved in a proximal direction.
Figure 6:
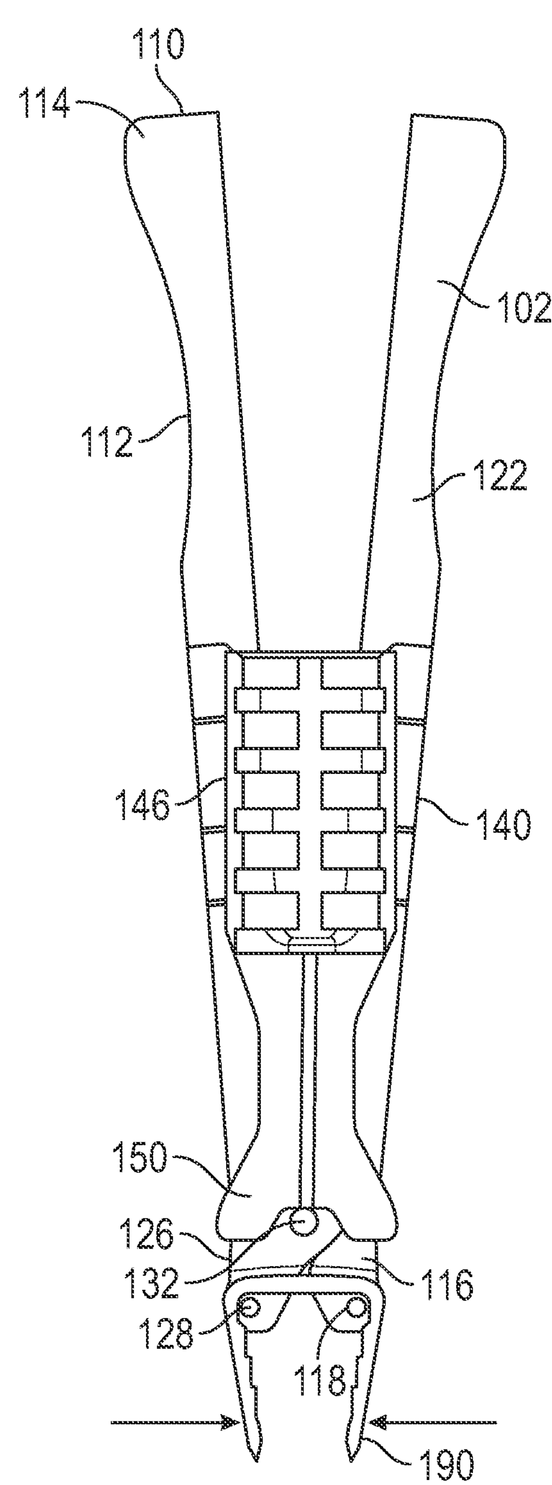
FIG. 6 is a top plan view of the staple inserter kit of FIG. 1, with the inserter moved to a staple release position.

Slider 140 further includes a distal portion 150 that is configured to cover pins 118, 128 in a staple securing position, shown in FIG. 5, and to expose pins 118, 128 when slid to a distal, staple release position, as shown in FIG. 6.

A staple 190 is disposed over the first pin 118 and the second pin 128. Staple 190 has a first arm 192 with barbs 193, a second arm 194 with barbs 195, and a bridge 196 connecting the first arm 192 and the second arm 194. First arm 192 and second arm 194 are naturally biased toward each other.

Staple 190 is mounted over pins 118, 128 and is configured to slide off the pins 118, 128 when the slider 140 is in the staple release position, shown in FIG. 6. The first pin 118 is at a connection between the first arm 192 and the bridge 196 and the second pin 128 is at a connection between the second arm 194 and the bridge 196. The first and second arms 192, 194 are based away from each other when the slider 140 is in the staple securing position, as shown in FIG. 5.

A staple drill guide 200 is shown in FIGS. 12-15. Guide 200 is used to properly space openings for staple arms 192, 194 in bone portions 50, 52 (shown in FIGS. 7-11. Guide 200 includes a body 210 having a proximal end 212 and a distal end 214. Proximal end 212 is a handle that the clinician uses to hold guide 200, while distal end 214 includes a pair of parallel, spaced guide tubes 220, 222. Guide tubes 220, 22 are used to align a drill (not shown) to drill staple holes in each of bones portions 50, 52.

To insert staple 190 into bone portions 50, 52, a clinician aligns staple drill guide 200 with bone portions 50, 52. The clinician then inserts a drill into each of guide tubes 220, 222 and drills holes in bone portions 50, 52. The clinician removes staple drill guide 200 and uses kit 100, with staple 190 pre-loaded onto inserter 102.

Staple 190 is positioned and inserted into holes in bone portions 50, 52. Next, slider 140 is slid distally in the direction of arrow "A" in FIG. 8. Next, proximal ends 114, 124 of handle arms 112, 122 are pivoted away from each other about pivot 132. This releases tension on staple arms 192, 194, allowing staple arms 192, 194 to attempt to bias toward each other. This bias feature draws bone portions 50, 52 toward each other to aid in connecting bone portions 50, 52 to each other.

Figure 11:
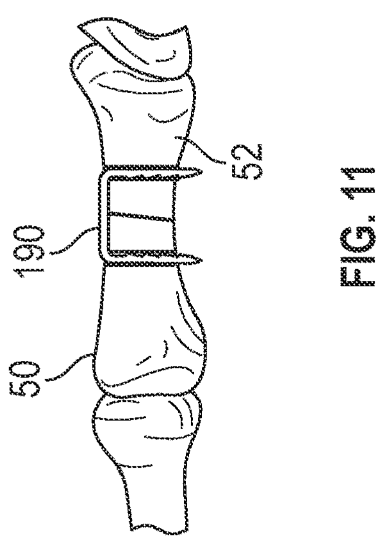
FIG. 11 is a side elevational view of the staple of the kit of FIG. 1 fully inserted into the bone portions.
Figure 10:
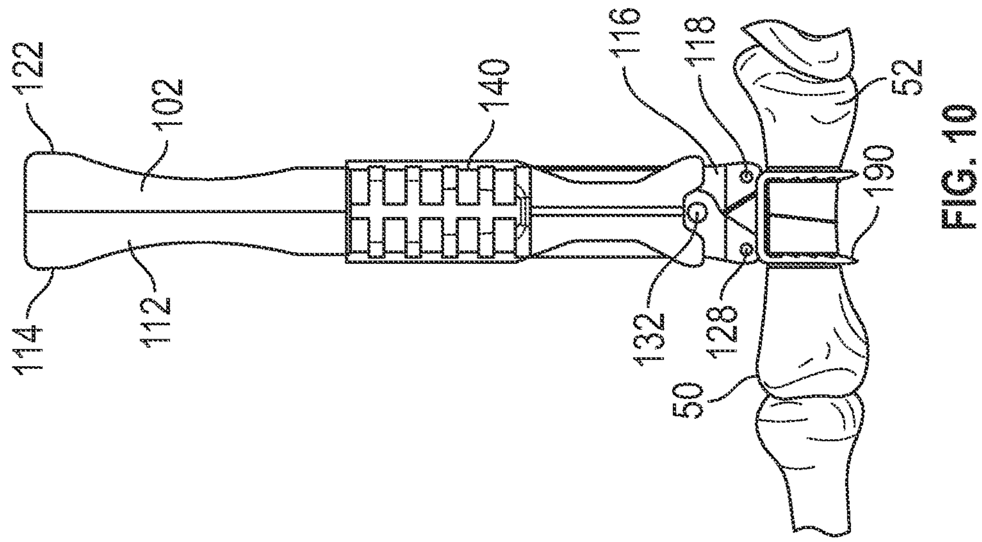
FIG. 10 is a side elevational view of the inserter kit of FIG. 1, with the inserter being used to tamp the staple into the bone portions.

Next, staple 190 is slid off pins 118, 128, as shown in FIG. 9. Optionally, staple 190 can be tamped into bone portions 50, 52 as shown in FIG. 10 to further secure staple 190. FIG. 11 shows staple 190 fully inserted into bone portions 50, 52.

Optionally, if desired or required, a second staple 190 can be reloaded onto inserter 102 and the second staple 190 can be inserted into the same bone portions 50, 52 at another location or into other bone portions using the same technique.

Figure 16C:
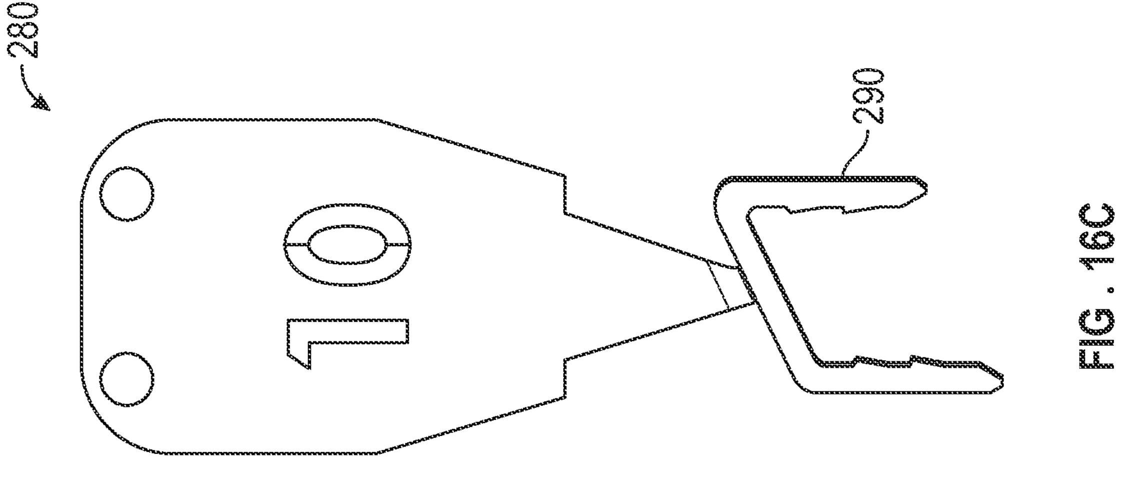
FIG. 16C is a front elevational view of a staple inserter kit according to another alternative exemplary embodiment of the present invention.
Figure 16B:
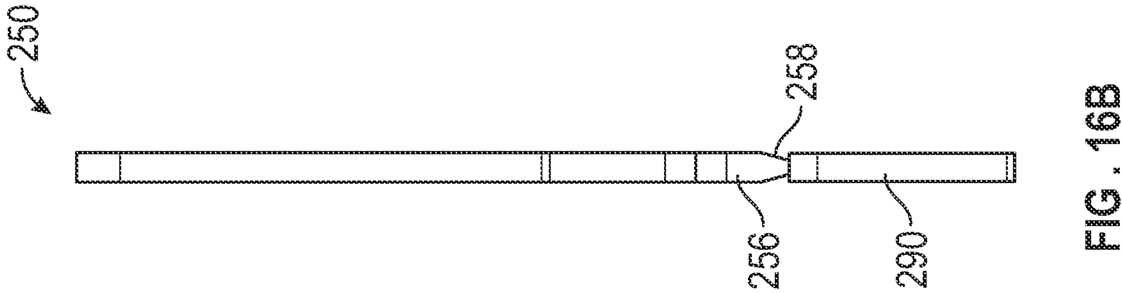
FIG. 16B is a side elevational view of the kit of FIG. 16A.
Figure 16A:
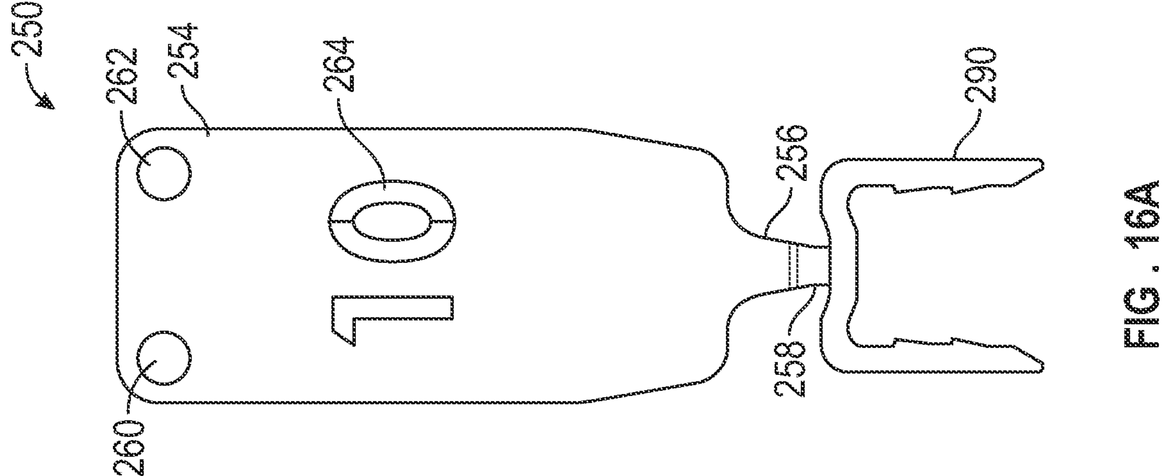
FIG. 16A is a front elevational view of a staple inserter kit according to an alternative exemplary embodiment of the present invention.
Figure 17:
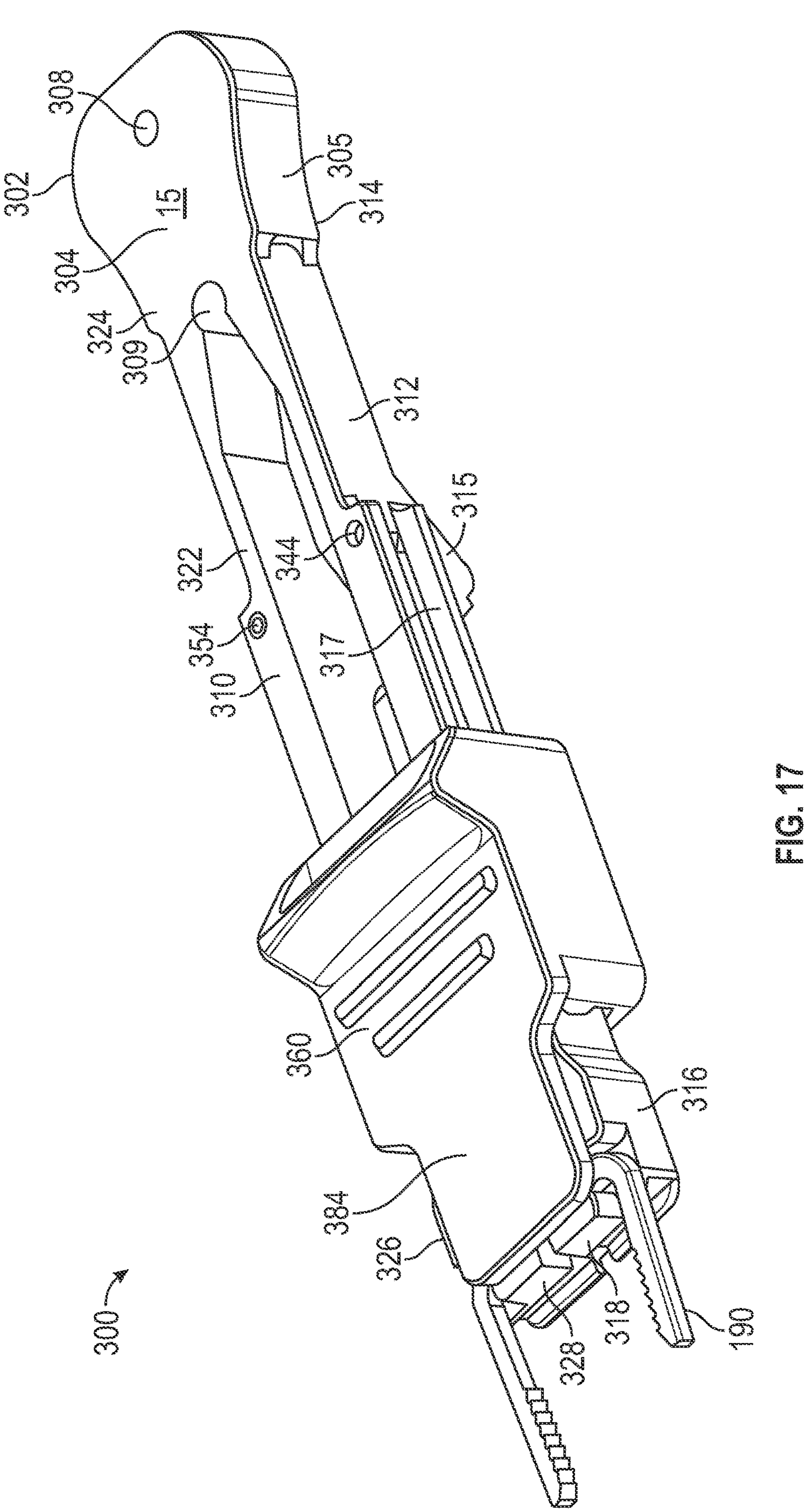
FIG. 17 is a perspective view of a staple inserter kit according to yet another exemplary embodiment of the present invention.

Alternative embodiments of a staple insertion kit 250, 280 are shown in FIGS. 16A-16C. Kit 250 includes a staple 290 fixedly attached to a distal end 256 of an inserter body 252. Inserter body 252 is generally flat with a relatively thin profile that is co-planar with a plane of staple 290, as shown in FIG. 16B.

A proximal end 254 of body 252 includes a pair of through holes 260, 262 that act as a staple drill template. Indicia 264 is provided to indicate a distance between though holes 260, 262. Distal end 256 of body 252 is narrowed, with a reduced cross section 258 to allow body 252 to be bent relative to staple 290 to remove body 252 from staple 290 after staple 290 is inserted into pre-drilled holes in bone portion 50, 52.

FIG. 16C shows kit 280, with an inserter body 282 extending in a plane that is oblique to a plane of staple 290. This oblique angle can provide better control for the clinician in certain circumstances, depending on the bone portions 50, 52 being stapled together.

FIGS. 17-37 show an alternative exemplary embodiment of a kit 300 that is used to insert a staple into adjacent bone portions. Similar to kit 100, kit 300 provides a staple and an inserter that is used to insert the staple into adjacent bones or adjacent bone fragments. Staple 190 can also be used in kit 300.

Referring specifically to FIGS. 20-23, inserter 302 includes an elongate handle 310 having a first handle arm 312 and a second handle arm 322. Indicia 304 is provided at a junction 305 of first handle arm 312 and second handle arm 322. Indicia 304 can be a number that indicates a bridge distance for the staple 190 that is used with inserter 302. Secondary through holes 308, 309 are formed at the junction 305 and are used to assist in aligning inserter 102 into its packaging for storage and shipment.

First handle arm 312 has a first proximal end 314 and a first distal end 316, distal from the first proximal end 314. A finger rest 315 is located on an underside of first arm 312 between proximal end 312 and distal end 314. A first pin or boss 318 extends outwardly from the first distal end 316. The first handle arm 312 also includes a slot 317 that extends along the side of first handle 310.

Similarly, second handle arm 322 has a second proximal end 324 and a second distal end 326, distal from the second proximal end 324. A finger rest 325 is located on an underside second arm 322 between proximal end 322 and distal end 324. A second pin or boss 328 extends outwardly from the second distal end 326. The second handle arm 322 also includes a slot 327 that extends along the side of second handle arm 320.

Figure 19:
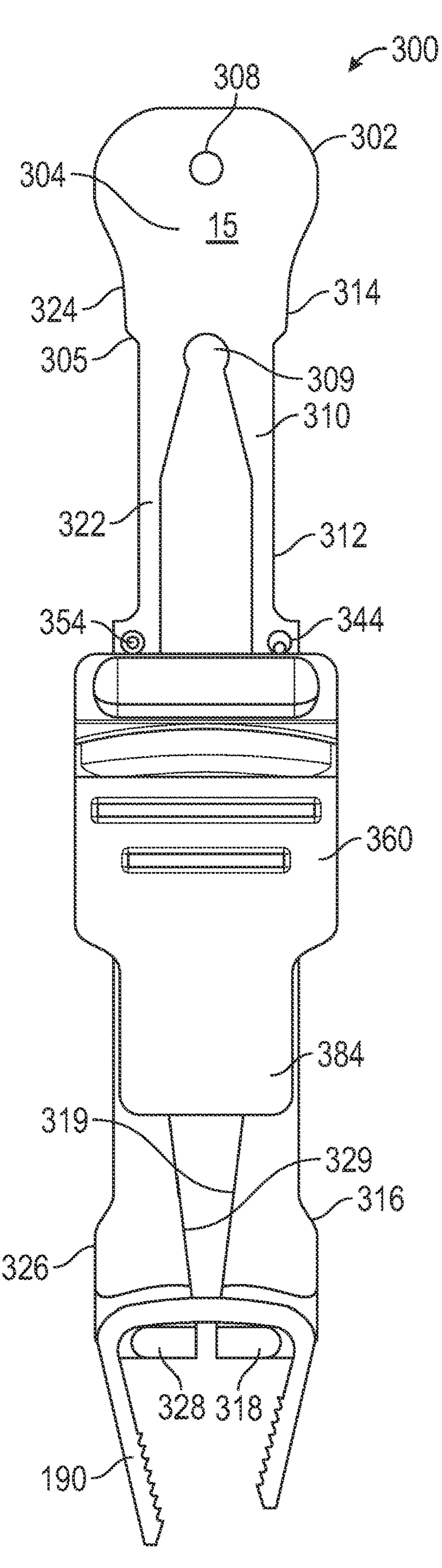
FIG. 19 is a is a top plan view of the kit of FIG. 17, with the slider in a staple release position.
Figure 20:
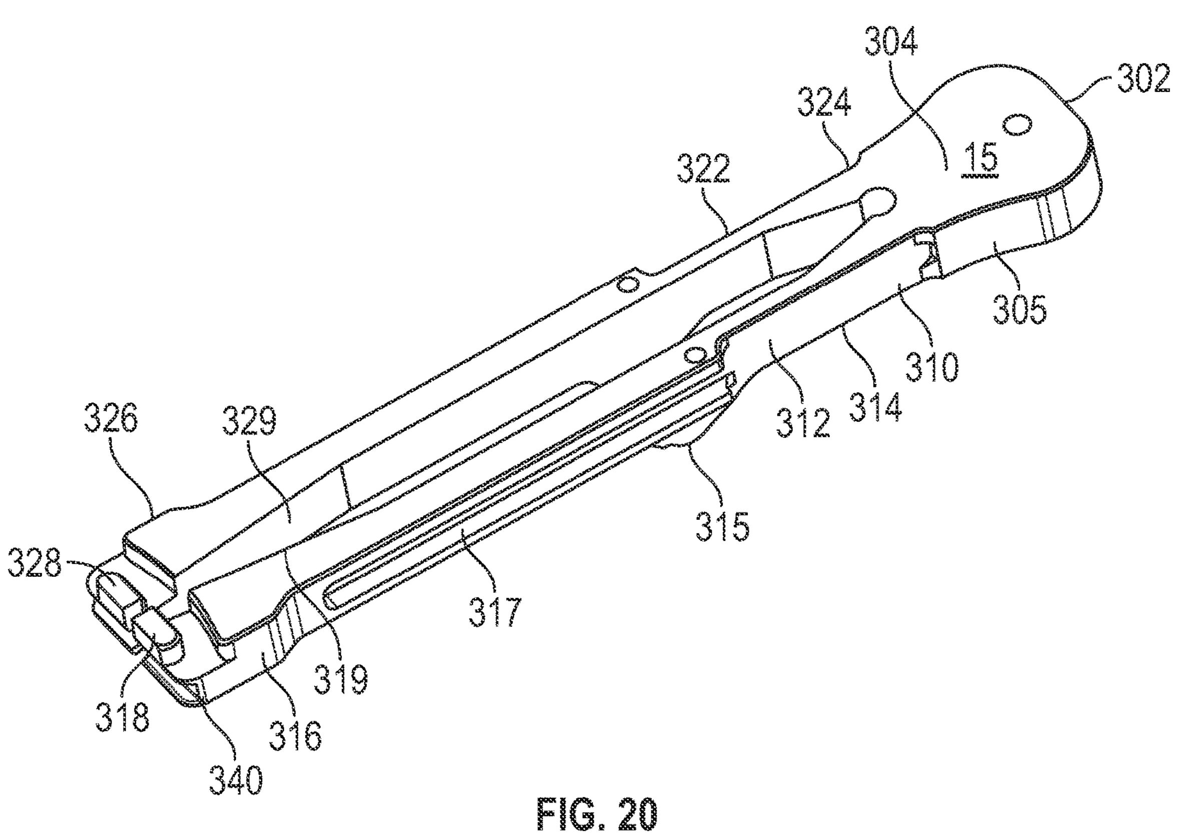
FIG. 20 is a perspective view of an inserter of the kit of FIG. 17.
Figure 21:
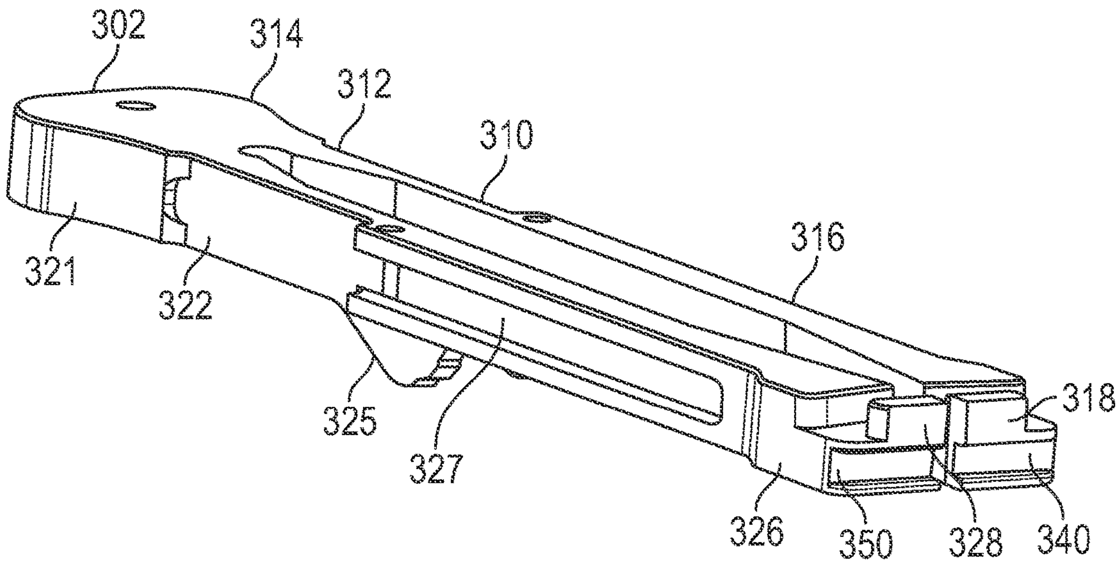
FIG. 21 is a different perspective view of the inserter of the kit of FIG. 17.
Figure 22:
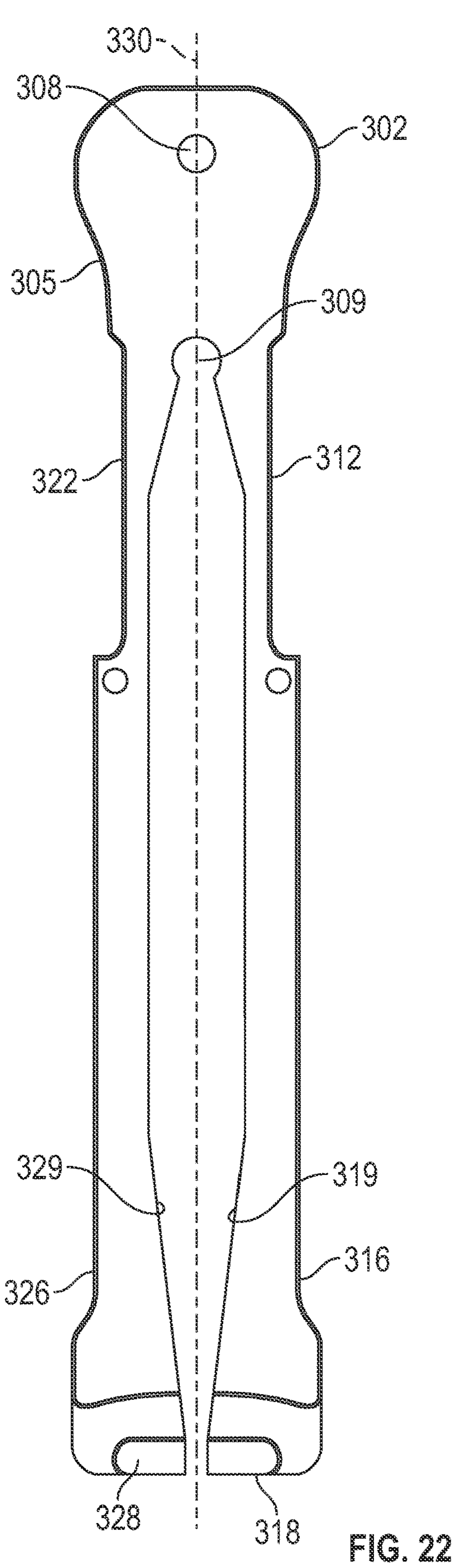
FIG. 22 is a top plan view of the inserter of FIG. 20.
Figure 23:
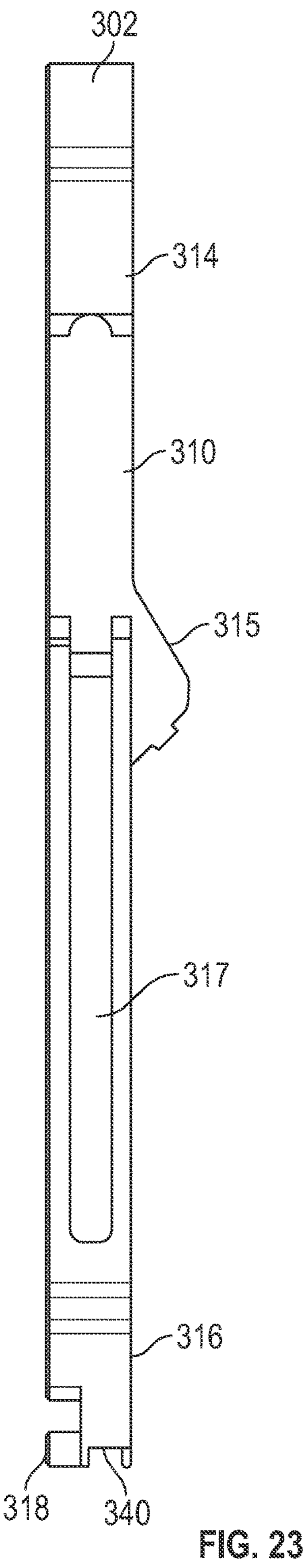
FIG. 23 is a side elevational view of the inserter of FIG. 20.
Figure 24:
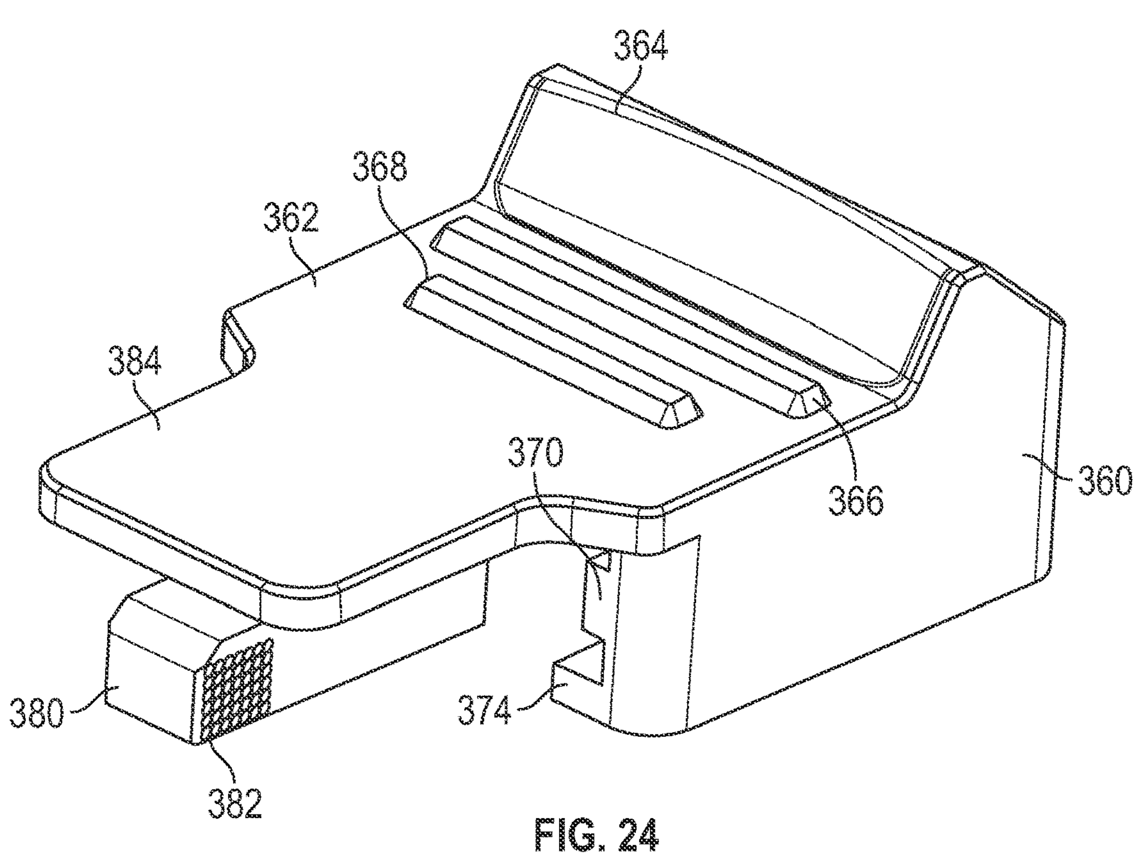
FIG. 24 is a front perspective view of the slider of the kit of FIG. 17.
Figure 25:
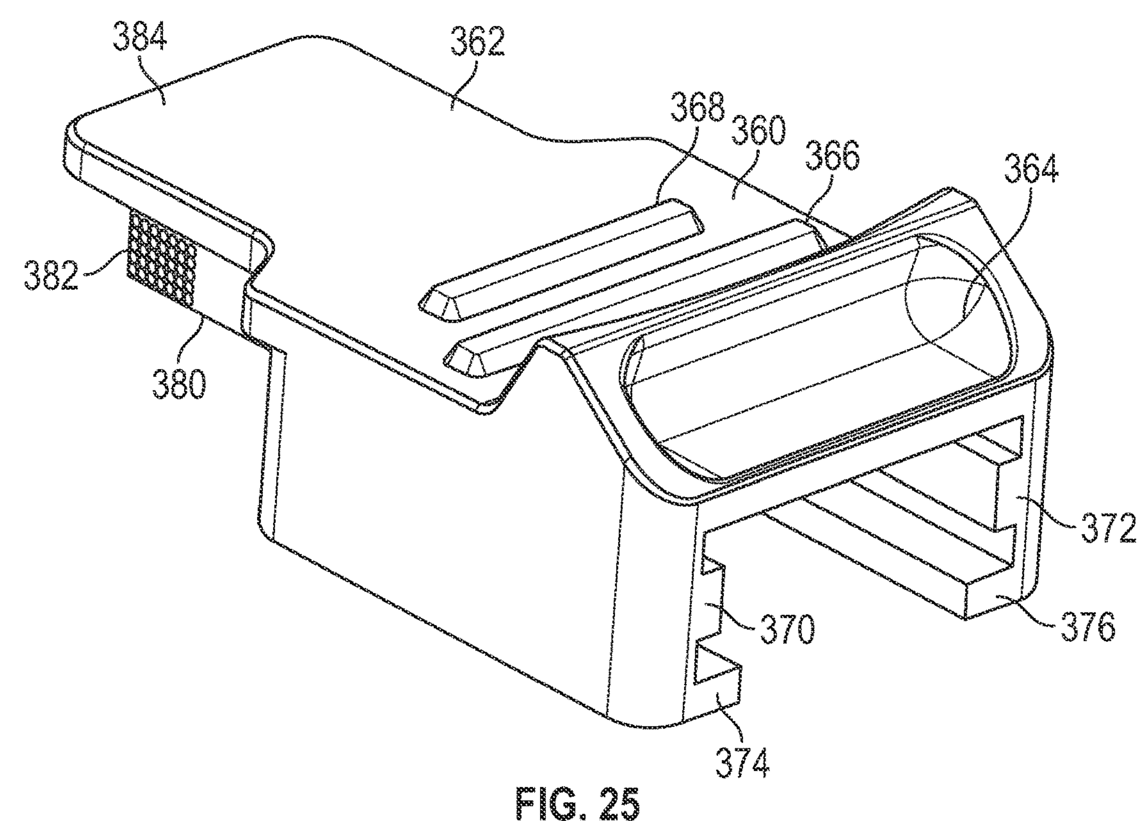
FIG. 25 is a left rear perspective view of the slider of FIG. 24.
Figure 26:
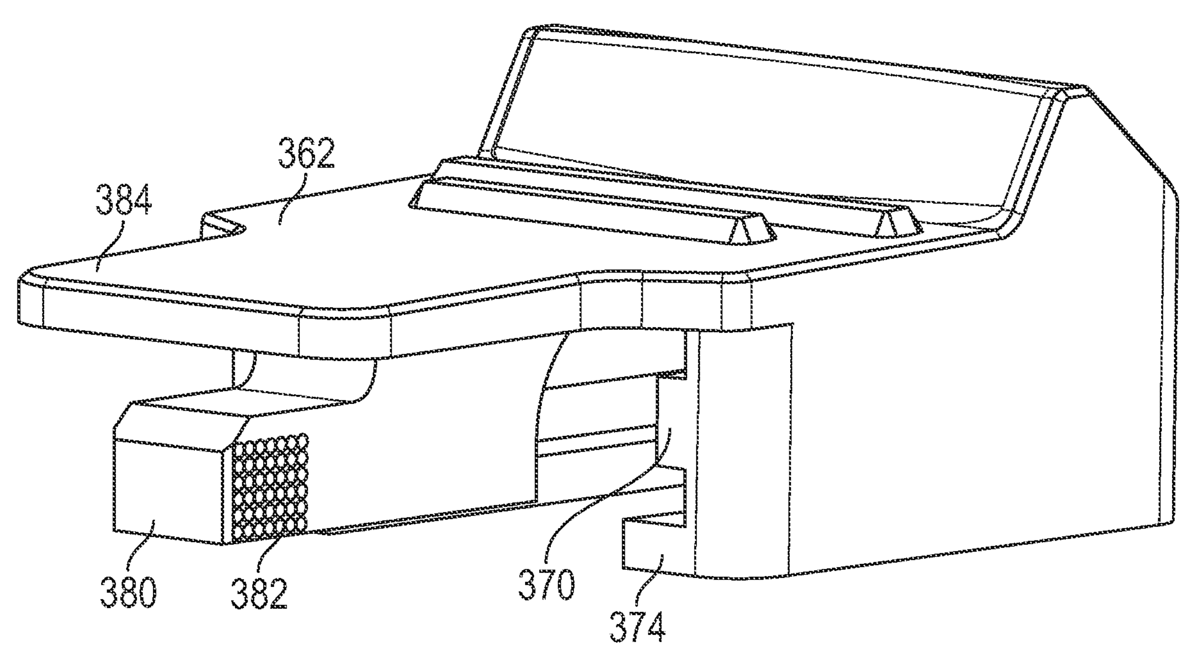
FIG. 26 is a right rear perspective view of the slider of FIG. 24.
Figure 27:
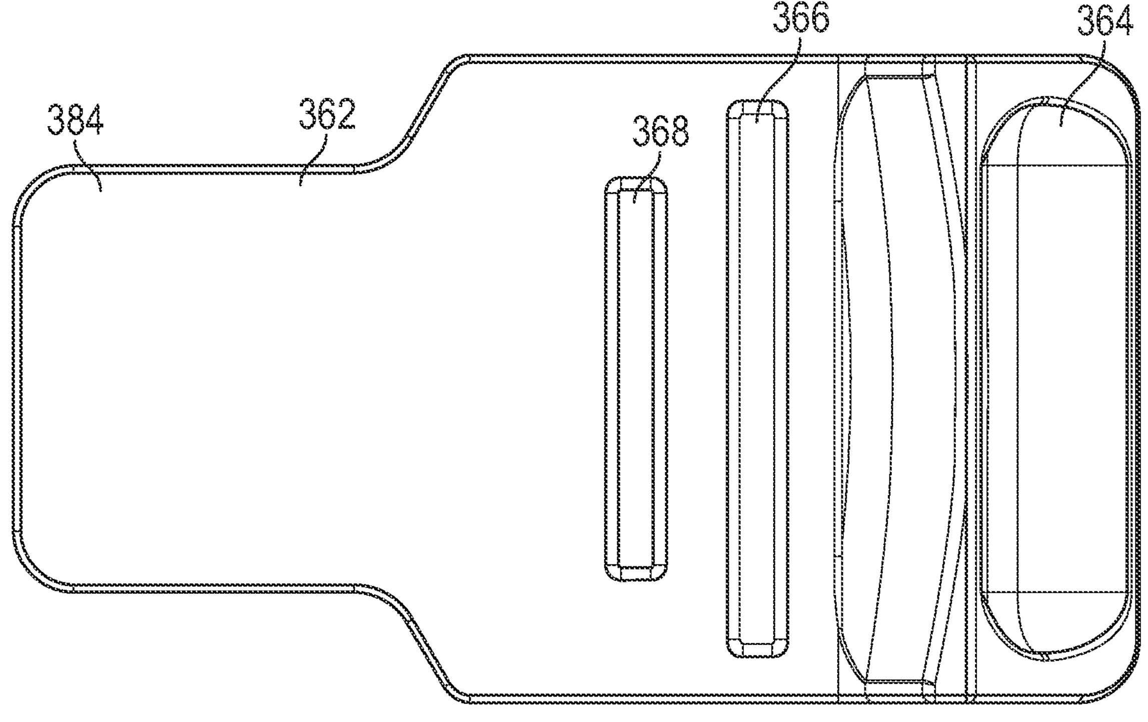
FIG. 27 is a top plan view of the slider of FIG. 14.
Figure 28:
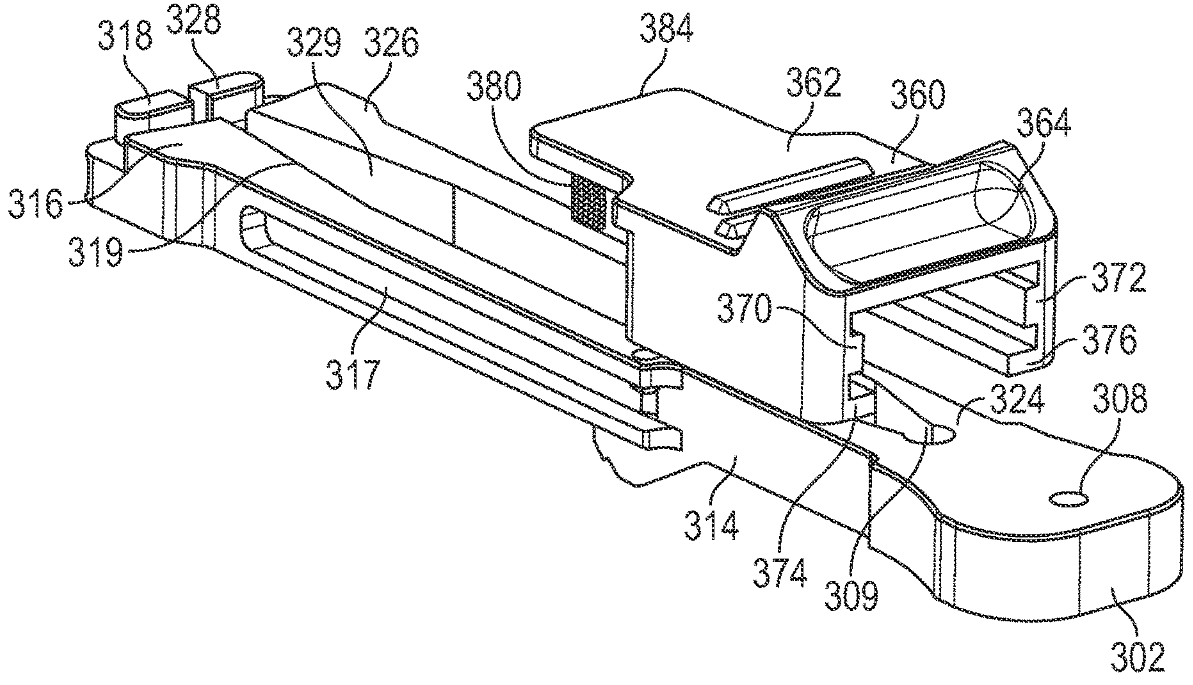
FIG. 28 is a perspective view of the slider of FIG. 24 being inserted onto the inserter of FIG. 20.

A central longitudinal axis 330 (shown in FIG. 22) extends between the first handle arm 312 and the second handle arm 322. The first handle arm 312 is attached to the second handle arm 322 at the first proximal end 314 and the second proximal end 324. Distal ends 316, 326 of handle arms 312, 322 converge toward longitudinal axis 330 in the form of ramps 319, 329, respectively, as shown in FIGS. 19 and 22 and are biased toward each other on opposing sides of longitudinal axis 330 such that boss 318 is biased away from boss 328. Distal ends 316, 326 converge toward longitudinal axis 330, as shown in FIG. 22.

Distal end 316, 326 of each arm 312, 322 also includes a tamper 340, 350. Tampers 340, 350 are parallel and co-planar with each other and are used to further insert staple 190 into the bone portions 50, 52 being connected by staple 190.

A slider 360 is slidingly attached to the handle 302. The slider 360 is used to move handle arms 312, 322 to spread and release staple arms 192, 194 for insertion into bone portions 50, 52 being stapled together.

Figure 18:
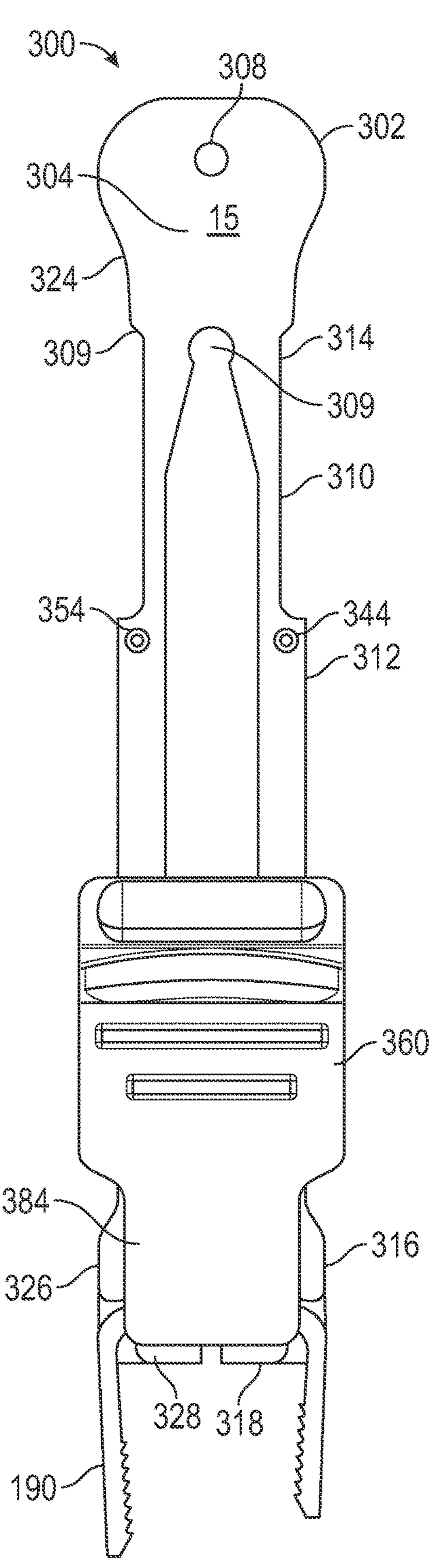
FIG. 18 is a top plan view of the kit of FIG. 17, with a slider in a staple pre-loaded position.

Slider 260 is movable between a staple securing position at the first distal end 316, as shown in FIG. 18, where the first proximal end 314 and the second proximal end 324 are biased away from each other and the first boss 318 is biased away from the second boss 328; and a staple release position, shown in FIG. 19, wherein the first distal end 316 and the second distal end 326 are biased toward each other and the first boss 318 is biased toward the second boss 328.

Referring specifically to FIGS. 24-27, slider 360 has a top surface 362 that includes a ramp 364 that a clinician's thumb can use to slide slider 360 from a proximal to distal direction along handle 302. Ramp 364 includes a concave, oblong surface to engage the thumb and reduce the risk of the thumb sliding off of ramp 394 while sliding ramp 364. Top surface 362 also includes two parallel raised ribs 366, 368 located distally of ramp 364 to provide a surface for the clinician's thumb to retract slider 360 from a distal to proximal direction to release staple 190 after staple 190 is inserted into bone portions 50, 52.

Figures 29, 30, 31:
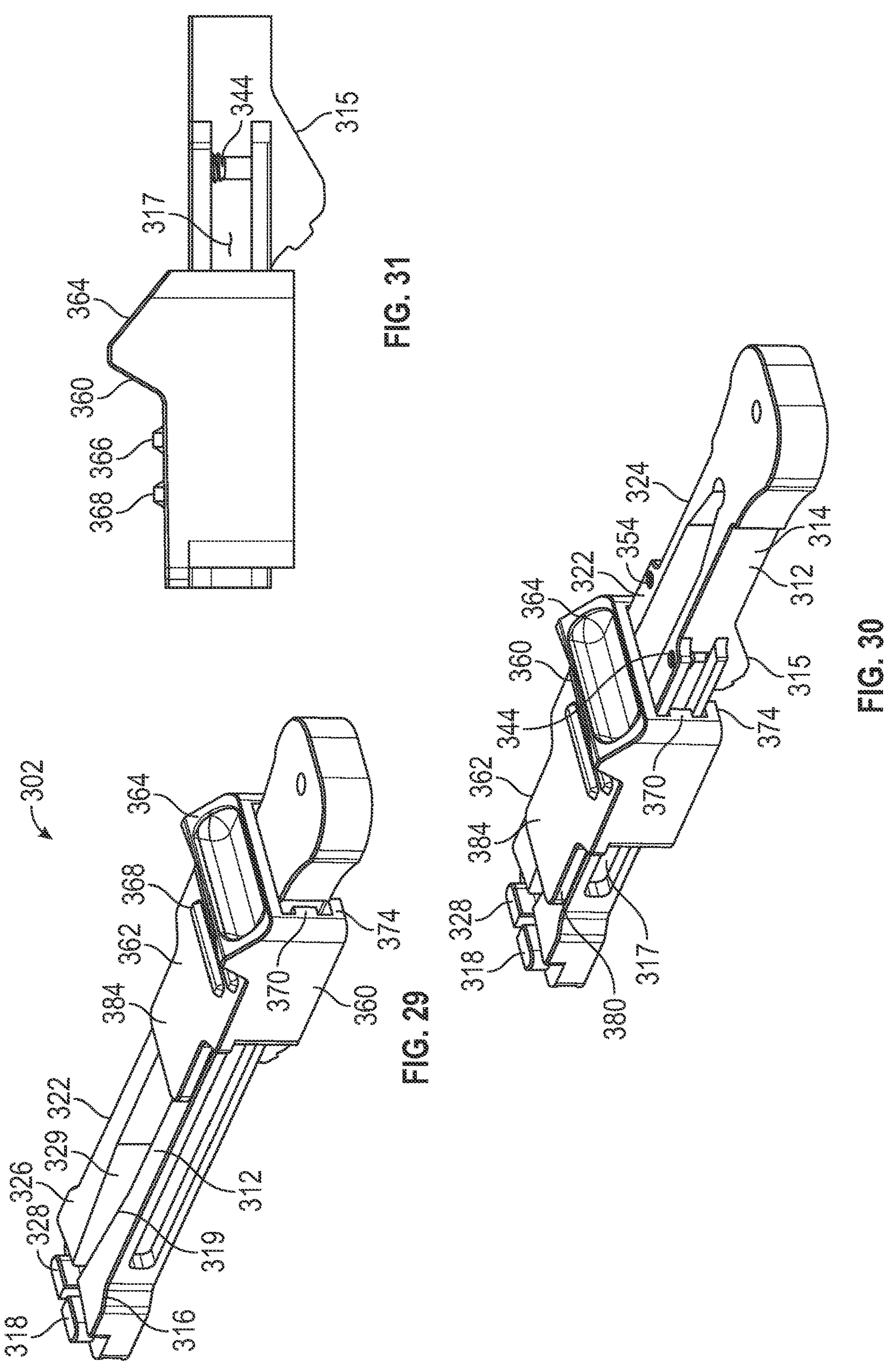
FIG. 29 is a perspective view of the slider of FIG. 24 inserted onto the proximal end of the inserter of FIG. 20.
FIG. 30 is a perspective view of the slider of FIG. 24 slid distally along the inserter of FIG. 20.
FIG. 31 is an enlarged side elevational view of the slider of FIG. 30 on the inserter of FIG. 30.

The slider 360 also includes side guides 370, 372 that are configured to ride along the slots 317, 327, respectively, as well as lower guides 374, 376, that are configured to ride under slots 317, 327, respectively, as shown in FIG. 30. Slider further uses a central wedge 380 extending distally and centered between guides 370, 372 and 374, 376. Wedge 380 is used to bias ramps 319, 329 apart from each other when slider 360 is slid distally along handle 302. Wedge 380 includes a plurality of nubs 382 that are provided on either side of wedge 380. Nubs 382 are used to provide a point contact between wedge 380 and ramps 319, 329 to reduce friction as slider 360 is slid along handle 302. In an exemplary embodiment, nubs 382 are formed in a two-dimensional 7×5 array, although those skilled in the art will recognize that other arrangements of nubs 382 can be provided. Slider 360 further includes a distal portion 384 that is configured to cover bosses 318, 328 in a staple securing position, shown in FIG. 18, and to expose bosses 318, 328 when slid to a distal, staple release position, as shown in FIG. 19.

To inserter slider 360 onto inserter 102, as shown in FIGS. 28-31 slider 360 is placed on handle 302 proximally of slots 317, 327 such that side guides 370, 372 are aligned with their respective slots 317, 327. Slider 360 is slid distally until slider 360 clears screw holes 342, 352 in arms 312, 322, as shown in FIG. 30. Self-tapping screws 344, 354 are inserted into screw holes 342, 352 to prevent slider 360 from sliding too far proximally and sliding out of slots 317, 327.

With inserter 302 fully assembled, staple 190 is attached to inserter 302. With slider 360 in a proximal position, staple 190 is placed over bosses 318, 328 such that first boss 318 is at a connection between the first arm 192 and the bridge 196 and wherein the second boss 328 is at a connection between the second arm 194 and the bridge 196, as shown in FIG. 19.

Staple 190 is disposed over the first boss 318 and the second boss 328. Staple 190 is configured to slide off the bosses 318, 328 when the slider 360 is in the staple release position, shown in FIG. 19. The first boss 318 is at a connection between the first arm 192 and the bridge 196 and the second boss 328 is at a connection between the second arm 194 and the bridge 196. The first and second arms 392, 394 are based away from each other when the slider 360 is in the staple securing position, as shown in FIG. 18.

To insert staple 190 into bone portions 50, 52 using inserter 302, a clinician aligns staple drill guide 200 with bone portions 50, 52. The clinician then inserts the drill into each of guide tubes 220, 222 and drills holes in bone portions 50, 52. The clinician removes staple drill guide 200 and uses kit 300, with staple 190 pre-loaded onto inserter 302 and slider 360 moved distally to bias staple legs 192, 194 away from each other for alignment into bone portions 50, 52.

Figures 32, 33, 34:
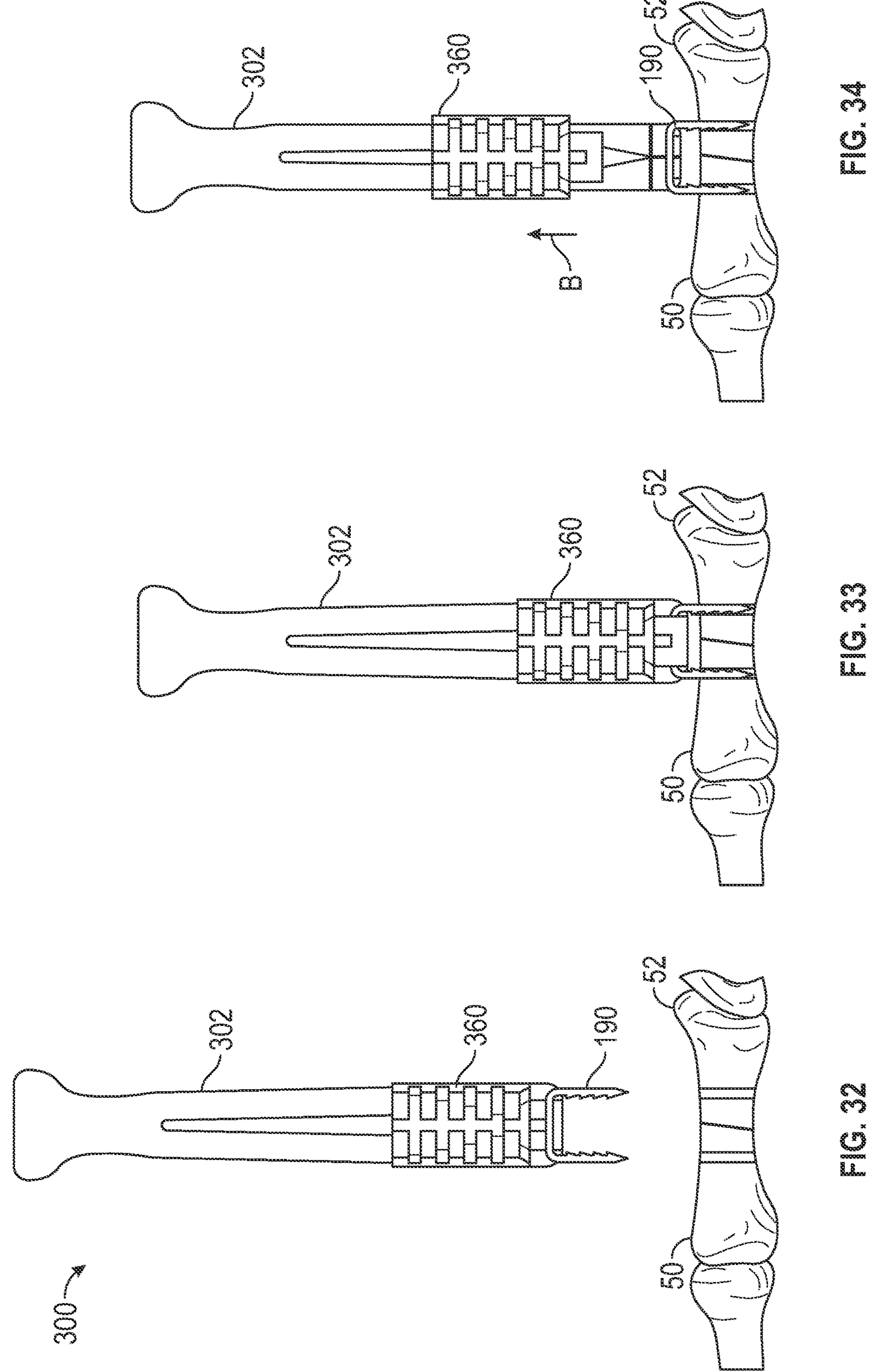
FIG. 32 is a side elevational view of the kit of FIG. 17 being inserted into two adjacent bone portions.
FIG. 33 is a side elevational view of the kit of FIG. 32, with the staple partially inserted into the bone portions.
FIG. 34 is a side elevational view of the kit of FIG. 32 with the slider being slid to a staple release position.

Staple 190 is positioned and inserted into holes in bone portions 50, 52 as shown in FIGS. 32 and 33. Next, as shown in FIG. 34, slider 360 is slid proximally in the direction of arrow "B". As slider 360 is slid proximally, distal ends 316, 326 of handle arms 312, 322 are allowed to compress toward each other. This releases tension on staple arms 192, 194, allowing staple arms 192, 194 to attempt to bias toward each other. This bias feature draws bone portions 50, 52 toward each other to aid in connecting bone portions 50, 52 to each other.

Next, inserter 302 is moved perpendicularly into the page of FIG. 34 and staple 190 is slid off bosses 318, 328 as shown in FIG. 35. Staple 190 can be tamped into bone portions 50, 52 as shown in FIG. 36 to further secure staple 190. To tamp staple 190, tampers 340, 350 are placed on top of bridge 196 and tampers 2340, 350 force staple legs 192, 194 into bone portions 50, 52 until bridge 196 is flush with the tops of bone portions 50, 52. FIG. 37 shows staple 190 fully inserted into bone portions 50, 52.

Optionally, if desired or required, a second staple 190 can be reloaded onto inserter 302 and the second staple 190 can be inserted into the same bone portions 50, 52 at another location or into other bone portions using the same technique.

Referring now to FIGS. 38-45 an alternative embodiment of a staple inserter kit 400 is shown. Kit 400 includes an elongate handle 402 having a handle proximal end 404 and a handle distal end 406, distal from the handle proximate end 404. A lever arm 410 has a lever proximal end 412 and a lever distal end 414, distal from the lever proximal end 412. The lever distal end 414 is attached to the handle distal end 406. The lever proximal end 412 is naturally biased away from the handle proximal end 404.

A first boss or pin 420 extends from the handle distal end 406 and a second boss or pin 422 extends from the lever distal end 404 toward the first pin 420. When the lever proximal end 412 is biased toward the handle proximal end 404, as shown by arrow "C" in FIG. 39, the first pin 420 and the second pin 422 are biased away from each other.

Staple 190 is disposed over the first pin 420 and the second pin 422. The first pin 420 is at a connection between the first arm 192 and the bridge 196 and the second pin 422 is at a connection between the second arm 194 and the bridge 196. First arm 192 and second arm 194 are biased toward each other in the direction of arrow "C" in FIG. 38.

Figures 38, 39:
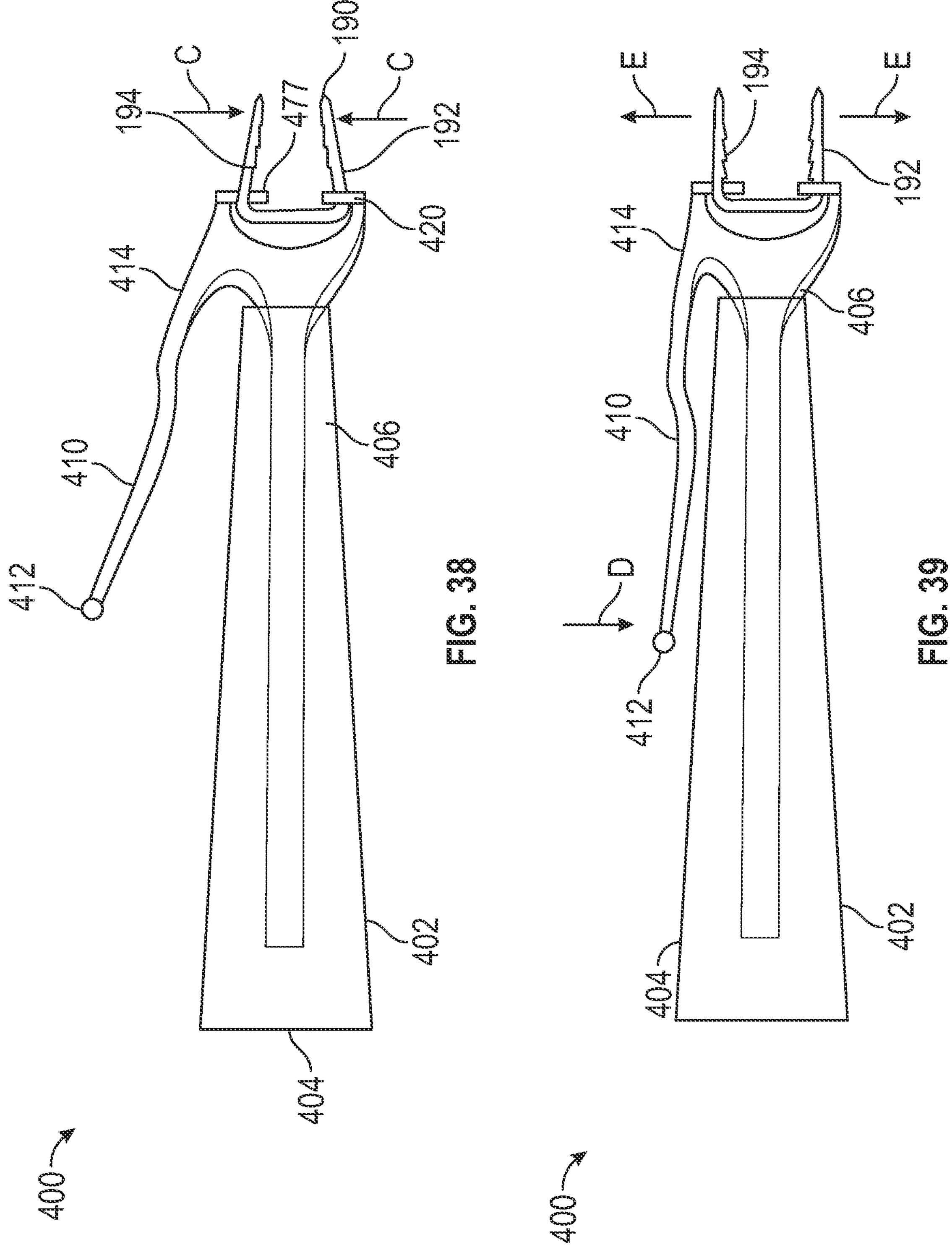
FIG. 38 is a top plan view of a staple inserter kit according to still another alternative exemplary embodiment of the present invention.
FIG. 39 is a top plan view of the kit of FIG. 38, with staple arms biased in an insertion position.
Figures 40, 41, 42:
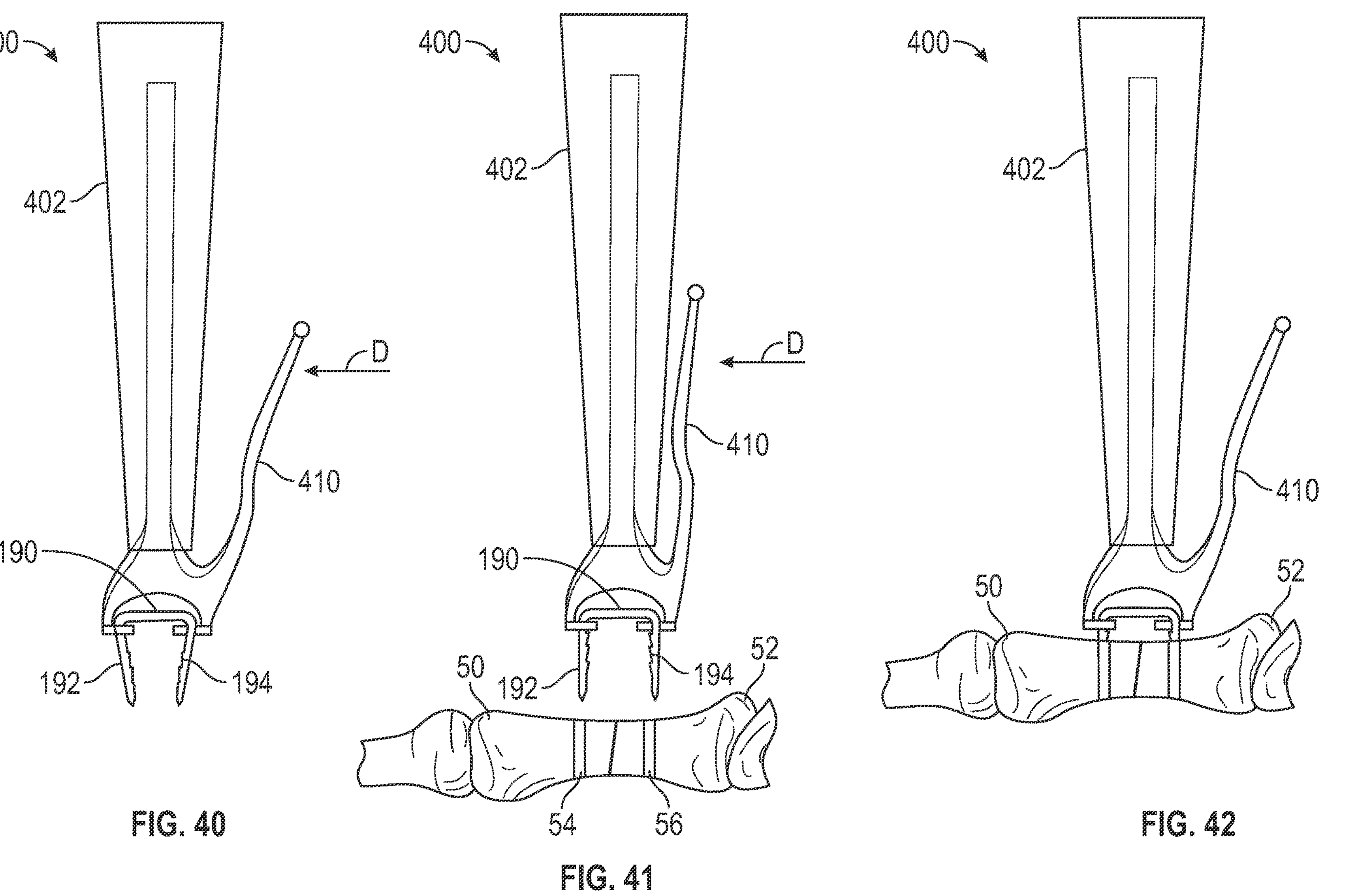
FIG. 40 is a side elevational view of the kit of FIG. 38, with the lever arm about to be biased to load the staple arms in an insertion position.
FIG. 41 is a side elevational view of the lever arm biasing the staple arms in the insertion position.
FIG. 42 is a side elevational view of the staple being inserted into bone portions and the lever arm being released.

To insert staple 190 using handle 402, as shown in FIG. 40, proximal end 412 of lever arm 410 is depressed toward proximal end 404 of handle 402 as shown in arrow "D", pulling pins 420, 422 away from each other and biasing staple legs 192, 194 apart from each other in the direction of arrows "E" as shown in FIG. 39. As shown in FIG. 41, staple arms 192, 194 are positioned at predrilled holes 54, 56 in adjacent bone portions 50, 52.

Figures 43, 44, 45:
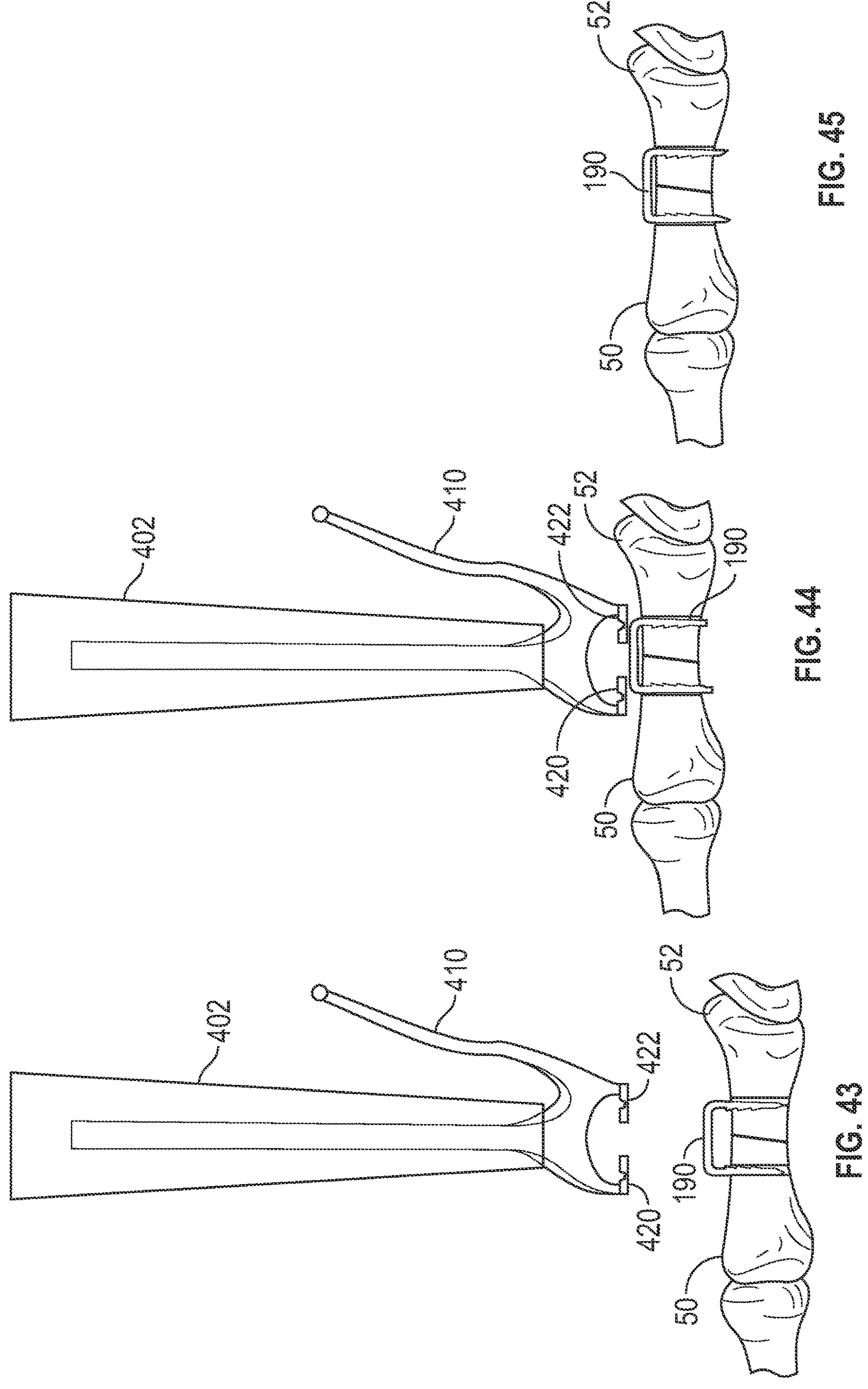
FIG. 43 is a side elevational view of the inserted being removed from the staple.
FIG. 44 is a side elevational view of the inserter being used to tamp the staple into the bone portions.
FIG. 45 is a side elevational view of the staple fully inserted into the bone portions.

Next, as shown in FIG. 42, handle 402 pushes staple 190 into bone portions 50, 50. FIG. 43 shows lever arm 410 released from handle 402, allowing staple legs 192, 194 to compress toward each other. Handle 402 is separated from staple 190 by sliding pins 420, 422 away from staple 190.

Next, as shown in FIG. 44, distal end 406 of handle 402 is used to tamp staple 190 all the way into bone portions 50, 52, with FIG. 45 showing staple 190 fully inserted into bone portion 50, 52.

It will be further understood that various changes in the details, materials, and arrangements of the parts which have been described and illustrated in order to explain the nature of this invention may be made by those skilled in the art without departing from the scope of the invention as expressed in the following claims.

We claim:

1. A compression staple insertion kit comprising:
an elongate handle comprising:
a first handle arm having:
a first proximal end;
a first distal end, distal from the first proximal end;
a first stopper between the first proximal end and the first distal end; and
a first boss extending outwardly from the first distal end;
a second handle arm having:
a second proximal end;
a second distal end, distal from the second proximal end; and
a second boss extending outwardly from the second distal end; and
a central longitudinal axis extending between the first handle arm and the second handle arm,
wherein the first handle arm is attached to the second handle arm at the first proximal end and the second proximal end;
a slider slidingly attached to the handle, the slider movable between:
a staple securing position at the first distal end, wherein the first distal end and the second distal end are biased away from each other and the first boss is biased away from the second boss; and
a staple release position toward the first proximal end,
wherein the stopper stops proximal movement of the slider, and
wherein the first distal end and the second distal end are biased toward from each other and the first boss is biased toward the second boss; and
a staple disposed around the first boss and the second boss, the staple having a first arm, a second arm, and a bridge connecting the first arm and the second arm, wherein the first boss is at a connection between the first arm and the bridge and wherein the second boss is at a connection between the second arm and the bridge.

2. The compression staple insertion kit according to claim 1, wherein the first proximal end is on a first side of the central longitudinal axis and the first distal end is on the first side of the central longitudinal axis.

3. The compression staple insertion kit according to claim 1, wherein the first handle arm comprises an elongate slot and wherein the slider comprises a guide configured to ride along the slot.

4. The compression staple insertion kit according to claim 3, wherein the slider further comprises a lower guide configured to ride underneath the slot.

5. The compression staple insertion kit according to claim 1, wherein the slider comprises a proximal ramp portion.

6. The compression staple insertion kit according to claim 1, wherein the first and second arms are based away from each other when the slider is in the staple securing position.

7. The compression staple insertion kit according to claim 1, wherein the staple is configured to slide off the bosses when the slider is in the staple release position.

8. The compression staple insertion kit according to claim 1, wherein an indicia is provided at a junction of the first handle arm and the second handle arm, wherein the indicia is a number that indicates a bridge distance for the staple.

9. The compression staple insertion kit according to claim 1, further comprising a first tamper at the first distal end and a second tamper at the second distal end.

10. The compression staple insertion kit according to claim 1, wherein the slider comprises a wedge located between the first handle arm and the second handle arm.

11. The compression staple insertion kit according to claim 10, wherein the wedge is configured to bias the first handle arm and the second handle arm away from each other when the slider is slid toward the first distal end and the second distal end.

12. The compression staple insertion kit according to claim 10, further comprising a plurality of nubs protruding from the wedge.

13. The compression staple insertion kit according to claim 1, wherein the slider further comprises a distal portion configured to cover the bosses in the staple securing position.

14. The compression staple insertion kit according to claim 1, further comprising a retaining screw in the handle, the screw configured to retain the slider on the handle.

15. The compression staple insertion kit according to claim 1, further comprising a staple drill guide, the staple drill guide comprising a body having a proximal end and a distal end, wherein the proximal end comprises a handle and wherein the distal end comprises a pair of parallel, spaced guide tubes.

16. A compression staple insertion kit comprising:

an elongate handle comprising:

a first handle arm having:

a first proximal end;

a first distal end, distal from the first proximal end; and a first boss extending outwardly from the first distal end;

a second handle arm having:

a second proximal end;

a second distal end, distal from the second proximal end; and a second boss extending outwardly from the second distal end; and a central longitudinal axis extending between the first handle arm and the second handle arm, wherein the first handle arm is attached to the second handle arm at the first proximal end and the second proximal end;

a slider slidingly disposed over the first handle arm and the second handle arm, the slider being movable between:

a staple securing position at the first distal end, wherein the first distal end and the second distal end are biased away from each other and the first boss is biased away from the second boss; and a staple release position toward the first proximal end, wherein the first distal end and the second distal end are biased toward each other and the first boss is biased toward the second boss; and a staple disposed around the first boss and the second boss, the staple having a first arm, a second arm, and a bridge connecting the first arm and the second arm, wherein the first boss is at a connection between the first arm and the bridge and wherein the second boss is at a connection between the second arm and the bridge.

17. The compression staple insertion kit according to claim 16, wherein the slider has a top surface and at least one rib formed on the top surface.

18. A compression staple insertion kit comprising:

an elongate handle comprising:

a first handle arm having:

a first proximal end;

a first distal end, distal from the first proximal end;

a first slot extending along an outer side of the first handle arm; and a first boss extending outwardly from the first distal end;

a second handle arm having:

a second proximal end;

a second distal end, distal from the second proximal end;

a second slot extending along an outer side of the second handle arm; and a second boss extending outwardly from the second distal end; and a central longitudinal axis extending between the first handle arm and the second handle arm, wherein the first handle arm is attached to the second handle arm at the first proximal end and the second proximal end;

a slider having a first slide guide engaged with the first slot and a second slide guide engaged with the second slot, the slider movable between:

a staple securing position at the first distal end, wherein the first distal end and the second distal end are biased away from each other and the first boss is biased away from the second boss; and a staple release position toward the first proximal end, wherein the first distal end and the second distal end are biased toward each other and the first boss is biased toward the second boss; and a staple disposed around the first boss and the second boss, the staple having a first arm, a second arm, and a bridge connecting the first arm and the second arm, wherein the first boss is at a connection between the first arm and the bridge and wherein the second boss is at a connection between the second arm and the bridge.

* * * * *